United States Patent [19]
Freiberg et al.

[11] Patent Number: 5,538,961
[45] Date of Patent: Jul. 23, 1996

[54] MACROCYCLIC LACTAM PROKINETIC AGENTS

[75] Inventors: Leslie A. Freiberg, Waukegan; Carla Edwards, Evanston; Richard J. Pariza, Winthrop Harbor; Hugh N. Nellans, Mundelein, all of Ill.

[73] Assignee: Abbott Laboratories, Abbott Park, Ill.

[21] Appl. No.: 108,659

[22] PCT Filed: Mar. 30, 1992

[86] PCT No.: PCT/US92/02590

§ 371 Date: Aug. 30, 1993

§ 102(e) Date: Aug. 30, 1993

[51] Int. Cl.$^6$ .................. C07D 225/02; C07D 413/14; A61K 31/33; A61K 31/395
[52] U.S. Cl. ................... 514/183; 540/457; 540/461; 540/463
[58] Field of Search .................. 540/454, 546, 540/457, 461, 463; 514/183

[56] References Cited

U.S. PATENT DOCUMENTS

| | | | |
|---|---|---|---|
| 5,189,159 | 2/1993 | Wilkening | 540/456 |
| 5,202,434 | 4/1993 | Wilkening | 546/454 |

*Primary Examiner*—John M. Ford
*Attorney, Agent, or Firm*—Thomas D. Brainard; Andreas M. Danckers

[57] ABSTRACT

Macrocylic lactam compounds of formula (I)

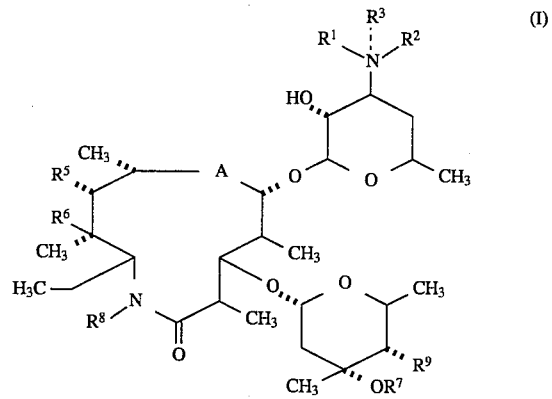

and pharmaceutically acceptable salts thereof, wherein A is selected from

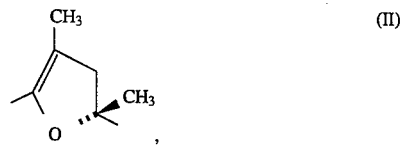

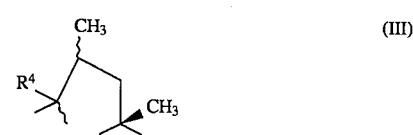

and

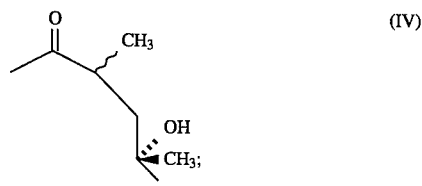

also disclosed are synthetic processes and intermediates useful in the preparation of the compounds of the invention, as well as compositions containing the same and methods for their use in stimulating contractile motion of the gastrointestinal tract.

7 Claims, No Drawings

MACROCYCLIC LACTAM PROKINETIC AGENTS

This is a 371 of PCT/US 92/02590, filed Mar. 30, 1992.

TECHNICAL FIELD

This invention relates to novel macrocyclic lactam derivatives of erythromycins A, B, C and D and pharmaceutical compositions containing these compounds, as well as the use thereof in treating gastrointestinal disorders and in facilitating the placement of diagnostic and therapeutic instrumentation into the proximal small intestine. The invention also relates to processes for preparing these compounds and synthetic intermediates employed therein.

BACKGROUND OF THE INVENTION

The primary function of the alimentary or gastrointestinal (GI) tract is to provide the body with a balanced supply of water, electrolytes and nutrients. In order for this to be achieved, food must be moved along the GI tract at an appropriate rate for digestion, absorption and secretion to take place. Food is normally transported through the GI tract in a well-coordinated manner by propulsive movements which are mediated by clusters of smooth muscle contractions known as migrating myoelectric complexes, in a process commonly referred to as peristalsis.

Defects in the normal motility pattern can lead to the development of chronic, painful and debilitating disorders. For example, an incompetent or weak lower esophageal sphincter may result in frequent reflux of ingested food from the stomach into the esophagus which may lead to esophagitis. Prokinetic agents (also called motility-enhancing agents) are useful in treating reflux esophagitis because they (a) increase the pressure of the lower esophageal sphincter, thereby inhibiting reflux; (b) increase the force of esophageal peristalsis to facilitate clearance of food from the esophagus into the stomach; and (c) increase gastric emptying, thereby further decreasing the mass available for reflux.

There is a need, however, for improved prokinetic agents in the treatment of this disorder. Presently used cholinergic drugs such as bethanechol and dopamine receptor blocking agents such as metoclopramide may exhibit serious disadvantages. Bethanechol, for example, should be avoided by elderly patients while metoclopramide has a narrow therapeutic index, pronounced central nervous system (CNS) side effects and is known to stimulate prolactin release.

Patients suffering from other GI motility-related disorders such as delayed gastric emptying, diabetic gastroparesis, anorexia, gall bladder stasis, surgically induced adynamic ileus and chronic constipation (colonic inertia) may also benefit from treatment with prokinetic agents. In addition, prokinetic agents can aid in the placement of diagnostic and therapeutic instrumentation, such as during the insertion of enteral feeding tubes into the proximal small intestine.

Another, less common but very painful and disruptive GI motility disorder is chronic intestinal pseudoobstruction. Patients who are severely afflicted with this problem cannot tolerate oral feedings and require total parenteral nutrition. Metochlopramide and bethanecholine are also used in the treatment of this disorder but often with disappointing results. Prokinetic agents could not only be useful in alleviating the distress associated with this disorder, but also in severe cases could be used to facilitate treatment by decompression of the upper GI tract by nasogastric tubal aspiration. Increased gastric motility brought about by the use of a prokinetic agent has been shown to facilitate the placement of the necessary tubes into the intestine.

Macrocyclic lactone (macrolide) prokinetic agents are known. For example, J. S. Gidda et al, in European Patent Application No. 0349100, published Jan. 3, 1990, disclose 12-membered macrolides for use as gastrointestinal motility enhancers. S. Omura and Z. Itoh, in U.S. Pat. No. 4,677,097, issued Jun. 30, 1987, European Application No. 215,355, published Mar. 25, 1987, and European Application No. 213,617, published Mar. 11, 1987, disclose derivatives of erythromycins A, B, C and D which are useful as stimulants of digestive tract contractile motion. However, the compounds of these references are distinct from those of the present invention, in which novel lactam derivatives of the erythromycins are disclosed which possess an unexpected degree of prokinetic activity.

SUMMARY OF THE INVENTION

In one aspect of the present invention are provided macrocylic lactam prokinetic agents of formula (I)

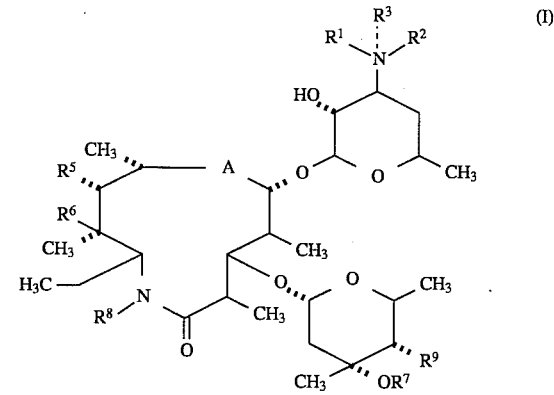

and pharmaceutically acceptable salts thereof wherein the dotted line is an optional bond. In formula (I), A is selected from

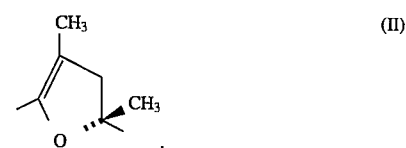

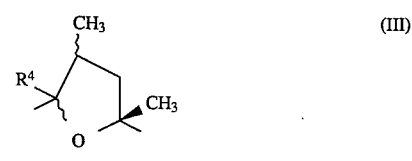

and

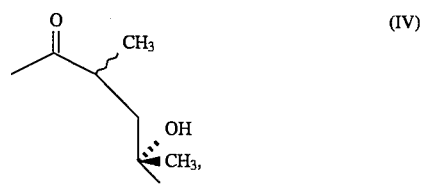

where a wavy line represents a bond having either steric orientation.

$R^1$ and $R^2$ in formula (I) may independently be selected from hydrogen, loweralkyl, halo-substituted loweralkyl, cyano-substituted loweralkyl, hydroxy-substituted loweralkyl, loweralkenyl, loweralkynyl, lower cycloalkyl, lower cycloalkylmethyl and benzyl.

$R^3$ in formula (I) may be absent or, if present, selected from loweralkyl, loweralkenyl, loweralkynyl and benzyl and accompanied by a pharmaceutically acceptable counterion so as to form a quaternary ammonium salt.

$R^4$ in formulae (I) and (III) may be hydrogen or, taken together with $R^6$, may form an ether bridge.

$R^5$ in formula (I) may be —OH, or —$OR^{10}$, wherein $R^{10}$ is selected from loweralkyl, loweralkanoly and —$S(O)_2CH_3$, or, taken together with $R^6$ and the carbons to which they are attached, may form a cyclic carbonate.

$R^6$ in formula (I) may be hydrogen, —OH, or —$OR^{11}$ wherein $R^{11}$ is selected from loweralkyl, loweralkanoly and —$S(O)_2CH_3$; or, taken together with $R^4$, may form an ether bridge; or, taken together with $R^5$ and the carbons to which they are attached, may form a cyclic carbonate.

$R^7$ in formula (I) may be either hydrogen or methyl.

$R^8$ in formula (I) may be hydrogen or loweralkyl.

$R^9$ in formula (I) may be hydrogen or hydroxy.

In another aspect of the present invention are provided synthetic processes for preparing the compounds of the invention, as well as novel intermediates of formulae (V) and (VI)

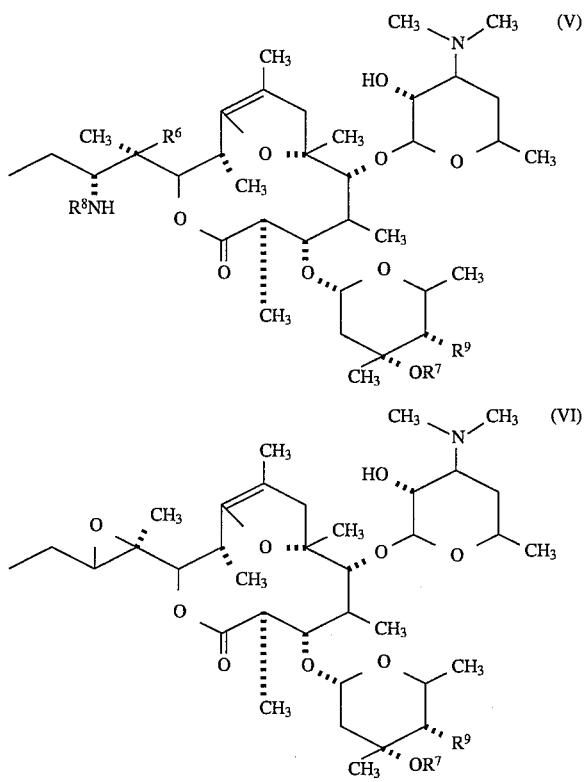

useful therein wherein $R^6$ is —OH or hydrogen, $R^7$ is hydrogen or methyl, $R^8$ is hydrogen or loweralkyl and $R^9$ is hydrogen or hydroxyl. The lactam compounds of the invention may be prepared directly from such intermediates, as by inducing ring closure of the amine alcohol of formula (V) or by an epoxide opening and spontaneous cyclization of the epoxide of formula (VI). Alternatively, the epoxide intermediate may first be converted to an azido alcohol and then reduced to the above amine alcohol before ring closure is induced.

In a further aspect of the present invention are provided pharmaceutical compositions for stimulating contractile motion of the gastrointestinal tract comprising a therapeutically effective amount of a compound of the invention and a pharmaceutically acceptable carrier.

In yet another aspect of the present invention is provided a method of treating disorders characterized by impaired gastrointestinal motility such as esophageal reflux, diabetic gastroparesis, pediatric gastroparesis, postoperative paralytic ileus, intestinal pseudoobstruction, gallbladder stasis, anorexia, gastritis, emesis and chronic constipation, comprising administering to a human or lower mammal in need of such treatment a therapeutically effective amount of a compound of the invention. In a related aspect, the present invention provides a method of facilitating the placement of diagnostic and therapeutic instrumentation, such as enteral feeding tubes, into the proximal small intestine comprising administering to a human or lower mammal in need of such treatment a therapeutically effective amount of an inventive compound.

DETAILED DESCRIPTION OF THE INVENTION

The present invention comprises novel compounds of formula (I) and the pharmaceutically acceptable salts thereof which are gastrointestinal prokinetic agents. The compounds of the present invention did not exhibit antibacterial activity in in vitro screening assays. These compounds are synthetic lactam derivatives of erythromycins A through D; accordingly, substituents $R^6$ and $R^7$ of the formulae herein are initially determined, as shown below, by the particular erythromycin used as starting material:

| Erythromycin | Resulting $R^6$ | Resulting $R^7$ |
|---|---|---|
| A | —OH | methyl |
| B | hydrogen | methyl |
| C | —OH | hydrogen |
| D | hydrogen | hydrogen |

However, such lactams may be further derivatized, using well-known synthetic methodology, to obtain compounds of the invention having other substituents $R^6$ as well.

One class of compounds of the present invention, formed when A of formula (I) is a group of formula (II), may be represented by the formula

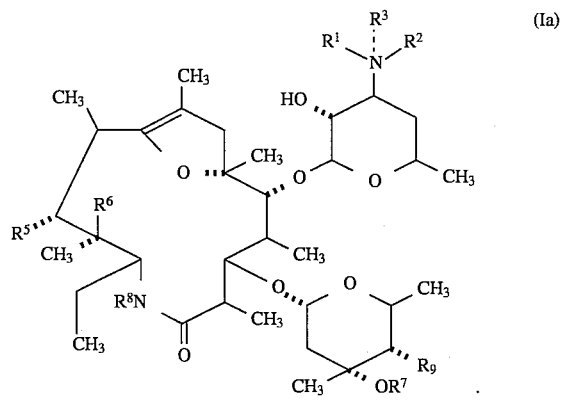

Another class of compounds of the invention, formed when A is a group of formula (III) in which $R^4$ is hydrogen, may be represented by the formula

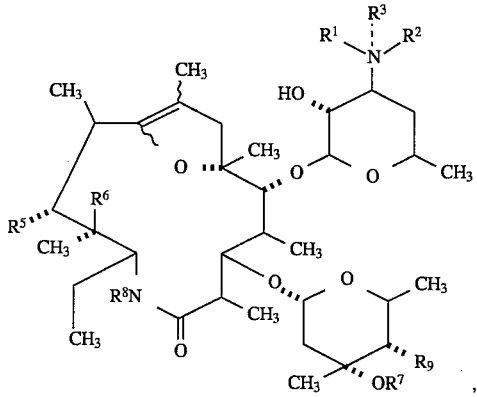

(Ib)

wherein, as elsewhere throughout this application, a wavy line represents a bond having either steric orientation.

A corresponding subclass of compounds of the invention occurs when $R^4$ of formula (III), together with $R^6$, forms an ether linkage; these compounds may be represented by the formula

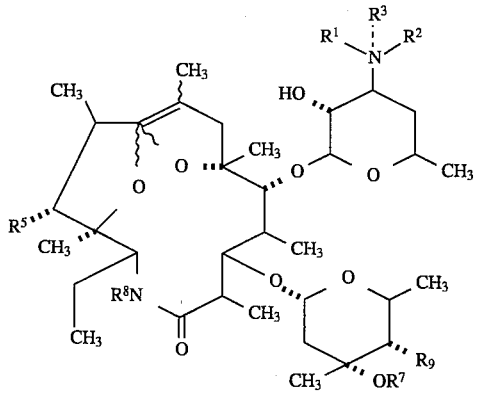

(Ic)

Yet another class of compounds of the present invention, formed when A is a group of formula (IV), may be represented by the formula

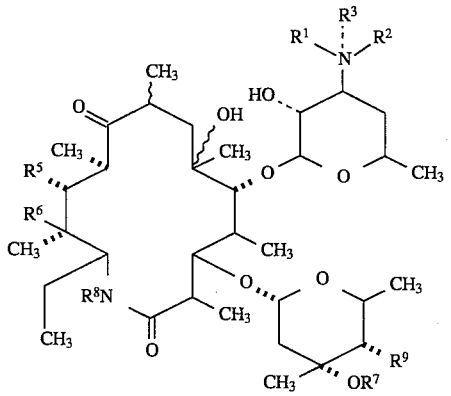

(Id)

Representative compounds of the present invention include

[2R-(2R*,3R*, 4R*,5R*,8R*,9S*, 10S*,11R*,12R*)]- 9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl-11-[[3,4,6-trideoxy-3-(dimethylamino)-β-D-xylo-hexopyranosyl]oxy]- 6-aza-15-oxabicyclo[10.2.1]pentadec-14-en-7-one ("erythromycin A lactam enol ether");

[2R-(2R*,3S*, 4S*,5R*,8R*,9S*,10S*, 11R*,12R*)]-9-[(2,6-Dideoxy-3-C-methyl-3-methyl-3-O-methyl-α-L-ribo-hexopyranosyl)oxy]- 5-ethyl-3-hydroxy-2,4,8,10,12,14-hexamethyl-11-[[3,4,6-trideoxy-3-(dimethylamino)-β-D-xylo-hexopyranosyl]oxy]-6-aza-15oxabicyclo[10.2.1]pentadec-14-en-7-one ("erythromycin B lactam enol ether");

[2R-(2R*,3R*, 4R*,5R*,8R*,9S*, 10S*,11R*,12R*)]-9-[(2,6-Dideoxy-3-C-methyl-3O-methyl-α-L-ribo-hexopyranosyl)oxy]- 5-ethyl-3,4-dihydroxy-2,4,8,10,12,14-hexamethyl- 11-[[3,4,6-trideoxy-3-(methylamino)-β-D-xylo-hexopyranosyl]oxy]- 6-aza-15-oxabicyclo[10.2.1]pentadec-14-en-7-one;

[2R-(2R*,3R*, 4R*,5R*,8R*,9S*,10S*, 11R*,12R*)]-9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(ethylmethylamino)-62 -D-xylo-hexopyranosyl]oxy]-6-aza-15-oxabicyclo [10.2.1]pentadec-14-en-7-one;

[2R-(2R*,3R*, 4R*,5R*,8R*,9S*,10S*, 11R*,12R*)]-9-[(2,6-Dideoxy-3-C-methyl-3-O-methyl-α-L-ribo-hexopyranosyl)oxy]- 5-ethyl-3,4-dehydroxy-2,4,8,10,12,14-hexamethyl- 11-[[3,4,6-trideoxy-3-(methyl(2-propenyl)amino)-β-D-xylo-hexopyranosyl]oxy]-6-aza-15-oxabicyclo[10.2.1]pentadec-14-en-7-one;

[2R-(2R*,3R*, 4R*,5R*,8R*,9S*,10S*, 11R*,12R*)]-9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(dimethyl(2-propenyl)ammonium)-62 -D-xylo-hexopyranosyl]oxy]-6-aza-15-oxabicyclo[10.2.1]pentadec-14-en-7-one bromide;

[2R-(2R*,3R*, 4R*,5R*,8R*,9S*, 10S*,11R12R*)]-9-[(2,6Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(dimethylamino)-β-D-xylo-hexopyranosyl]oxy]- 6-aza-15-oxabicyclo[10.2.1]pentadec-14-en-7-one 13-O-14-O-carbonate;

[1R-(1R*2R*,3R*, 4R*,5R*,8R*,9S*, 10S*,11R*,12R*,14S*)]- 2,6-Dideoxy-3-C-methyl-3-O-methyl-α-L-ribohexopyranosyl)oxy]- 5-ethyl-3,4-dihydroxy2,4,8,10,12,14-hexamethyl-11-[[3,4,6-trideoxy-3-(dimethylamino)-β-D-xylo-hexopyranosyl]oxy]-6-aza-15-oxabicyclo[10.2.1]pentadecan-7-one;

[1R-(1R*,2R*,3R*, 4R*,5R*,8R*,9S*, 10S*,11R*,12R*,+b 14S*)]-[(2,6-dideoxy-3-C-methyl- 3-O-methyl-α-L-ribo-hexopyranosyl)oxy]-5-ethyl-3-hydroxy-2,4,8,10,12,14-hexamethyl- 11-[[3,4,6-trideoxy-3-(dimethylamino)-β-D-xylo-hexopyranosyl]oxy]-6-aza- 15,16-dioxatricyclo[10.2.1.1$^{1,4}$]pentadecan-7-one;

[3R-(3R*, 4S*,5S*,6R*,7R*,9S*, 11R*,12R*,13R*,14R*)]- 4-[(2,6-dideoxy-3-C-methyl-3-O-methyl-α-L-ribohexopyranosyl)oxy]- 14-ethyl-7,12,13-trihydroxy-3,5,7,9,11,13-hexamethyl- 6-[[3,4,6-trideoxy-3-(dimethylamino)-β-D-xylo-hexopyranosyl]oxy] azacyclotetradecane-2,10-dione ("erythromycin A lactam");

[2R-(2R*,3R*, 4R*,5R*,8R*,9S*, 10S*,11R*,12R*)]-9-[(2,6-Dideoxy-3-C-methyl-α-L-ribo-hexopyranosyl)oxy]-5-ethyl-3,4-dihydroxy-2,4,8,10,12,14-hexamethyl-11-[[3,4,6-trideoxy-3-(dimethylamino)-β-D-xylo-hexopyranosyl]oxy]-6-aza-15oxabicyclo[10.2.1]pentadec-14-en-7-one ("erythromycin C lactam enol ether");

[2R-(2R*,3R*, 4R*,5R*,8R*,9S*, 10S*,11R*,12R*)]-9-[(2,6-Dideoxy-3-C-methyl-α-L-ribo-hexopyranosyl)oxy]-5-ethyl-3,4-dihydroxy-2,4,8,10,12,14-hexamethyl-11-[[3,4,6-trideoxy-3-(ethylmethylamino)-β-D-xylo-hexopyranosyl]oxy]-6-aza-15oxabicyclo[10.2.1]pentadec-14-en-7-one;

[2R-(2R*,3S*, 4S*,5R*,8R*,9S*, 10S*,11R*,12R*)]-9-[(2,6Dideoxy-3-C-methyl-α-L-ribo-hexopyranosyl)oxy]-5-ethyl-3-hydroxy-2,4,8,10,12,14-hexamethyl-11-[[3,4,6trideoxy-3-(dimethylamino)-β-D-xylo-hexopyranosyl]oxy]- 6-aza-15oxabicyclo[10.2.1]pentadec-14-en-7-one ("erythromycin D lactam enol ether");

[2R-(2R*,3S*, 4S*,5R*,8R*,9S*, 10S*,11R*,12R*)]-9-[(2,6-Dideoxy-3-C-methyl-α-L-ribo-hexopyranosyl)oxy]-5-ethyl-3-hydroxy-2,4,8,10,12,14-hexamethyl-11-[[3,4,6-trideoxy-3-(ethylmethylamino)-β-D-xylo-hexopyranosyl]oxy]- 6-aza-15oxabicyclo[10.2.1]pentadec-14-en-7-one;

[2R-(2R*,3R*, 4R*,5R*,8R*,9S*, 10S*,11R*,12R*)]-9-[(2,6-Dideoxy-3-C-methyl-3C-O-methyl-α-L-ribo-hexopyranosyl)oxy]- 5-ethyl-3,4-dihydroxy-2,4,6,8,10,12,14-heptamethyl- 11-[[3,4,6-trideoxy-3-(dimethylamino)-β-D-xylo-hexopyranosyl]oxy]- 6-aza-15-oxabicyclo[10.2.1]pentadec-14-en-7-one;

[2R-[2R*,3R*(1R*,2S *),6R*,7S*,8S*,9R*, 10R*]]-7-[(2,4,6-Trideoxy-3-C-methyl -3-O-methyl-α-L-ribo-hexopyranosyl)oxy]-3-(1,2-epoxy-1-methylbutyl)- 2,6,8,10,12-pentamethyl-9-[[2-O-acetyl- 3,4,6-trideoxy-3-(dimethylamino)-β-D-xylo-hexopyranosyl]oxy]-4,13-dioxabicyclo[8.2.1 ]tridec-12-en-5-one;

[2R-(2R*,3R*,4R*,5R*,8R*,9S*,10S*,11R*,12R*)]-9-[(2,4,6-Trideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(dimethylamino)-β-D-xylo-hexopyranosyl]oxy]-6-aza-15-oxabicyclo[10.2.1]pentadec-14-en-7-one;

[2R-(2R*,3R*,4R*,5R *,8R *,9S*,10S*,11R*,12R *)]-9-[(2,4,6-Trideoxy-3-C-methyl-3-O- methyl-α-L-ribo-hexopyranosyl)oxy]-5-ethyl-3,4-dihydroxy-2,4,6,8,10,12,14-heptamethyl- 11-[[3,4,6-trideoxy-3-(dimethylamino)-β-D-xylo-hex opyranosyl]oxy]- 6-aza- 15-oxabicyclo[10.2.1]pentadec-14-en-7-one;

[2R-(2R*,3R*,4R*,5R*,8R*,9S*,10S*,11R*,12R*)]-9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(n-butylmethylamino)-β-D-xylo-hexopyranosyl]oxy]-6-aza-15-oxabicyclo[10.2.1]pentadec-14-en-7-one;

[2R-(2R*,3R*,4R*,5R*,8R*,9S*,10S*,11R*,12R*)]-9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(n-propylmethylamino)-β-D-xylo-hexopyranosyl]oxy]-6-aza- 15-oxabicyclo[10.2.1]pentadec-14-en-7-one;

[2R-(2R *,3R*,4R*,5R*,8R*,9S*,10S *,11R*,12R*)]-9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(i-propylmethylamino)-β-D-xylo-hexopyranosyl]oxy]-6-aza-15-oxabicyclo[10.2.1]pentadec-14-en-7-one; and

[2R-(2R*,3R*,4R*,5R*,8R*,9S*,10S*,11R*,12R*)]-9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(i-butylmethylamino)-β-D-xylo-hexopyranosyl]oxy]-6-aza-15-oxabicyclo[10.2.1]pentadec-14-en-7-one;

as well as pharmaceutically acceptable salts thereof.

Preferred compounds of the present invention include

[2R-(2R*,3R*, 4R*,5R*,8R*,9S*, 10S*,11R*,12R*)]-9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(dimethylamino)-β-D-xylo-hexopyranosyl]oxy]- 6-aza-15oxabicyclo[10.2.1]pentadec-14-en-7-one ("erythromycin A lactam enol ether");

[2R-(2R*,3S*, 4S*,5R*,8R*,9S*, 10S*,11R*,12R*)]-9-[(2,6-Dideoxy-3-C-methyl-3-O-methyl-α-L-ribo-hexopyranosyl)oxy]- 5-ethyl-3-hydroxy-2,4,8,10,12,14-hexamethyl11-[[3,4,6-trideoxy-3-(dimethylamino)-β-D-xylo-hexopyranosyl]oxy]-6-aza- 15oxabicyclo[10.2.1]pentadec-14-en-7-one ("erythromycin B lactam enol ether");

[2R-(2R*,3R*, 4R*,5R*,8R*,9S*, 10S*,11R*,12R*)]-9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(methylamino)-β-D-xylo-hexopyranosyl]oxy]- 6-aza-15-oxabicyclo[10.2.1]pentadec-14-en-7-one;

[2R-(2R*,3R*, 4R*,5R*,8R*,9S*, 10S*,11R*,12R*)]-9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(ethylmethylamino)-β-D-xylo-hexopyranosyl]oxy]6-aza-15-oxabicyclo[10.2.1]pentadec-14-en-7-one;

[2R-(2R*,3R*, 4R*,5R*,8R*,9S*, 10S*,11R*,12R*)]-9-[(2,6-Dideoxy-3-C-methyl-O-methyl-α-L-ribo-hexopyranosyl)oxy]- 5-ethyl-3,4-dihydroxy-2,4,8,10,12,14-hexamethyl- 11-[[3,4,6-trideoxy-3-(dimethyl(2-propenyl)ammonium)-β-D-xylo-hexopyranosyl]oxy]-6-aza-15-oxabi-cyclo[10.2.1]pentadec-14-en-7-one bromide;

[2R-(2R*,3R*, 4R*,5R*,8R*,9S*, 10S*,11R*,12R*)]-9-[(2,6-Dideoxy-3-C-methyl-3-O-methyl-α-L-ribo-hexopyranosyl)oxy]- 5-ethyl-3,4-dihydroxy-2,4,6,8,10,12,14-heptamethyl- 11-[[3,4,6-trideoxy-3-(dimethylamino)-β-D-xylo-hexopyranosyl]oxy]- 6-aza- 15-oxabicyclo[10.2.1]pentadec-14-en-7-one;

[2R-(2R*,3R*,4R*,5R*,8R*,9S*, 10S*,11R*,12R*)]-9-[(2,4,6-Trideoxy-3-C-methyl-3-O-methylα-L-ribo-hexopyranosyl)oxy]- 5-ethyl-3,4-dihydroxy-2,4,8,10,12,14-hexamethyl- 11-[[3,4,6-trideoxy-3-(dimethylamino)-β-D-xylo-hexopyranosyl]oxy]- 6-aza-15-oxabicyclo[10.2.1]pentadec-14-en-7-one;

[2R-(2R*,3R*,4R*,5R*,8R*,9S*,10S*,11R*,12R*)]-9-[(2,4,6-Trideoxy-3-C-methyl-3-O-methyl-α-L-ribo-hexopyranosyl)oxy]- 5-ethyl-3,4-dihydroxy-2,4,6,8,10,12,14-heptamethyl- 11-[[3,4,6-trideoxy-3-(dimethylamino)-β-D-xylo-hexopyranosyl]oxy]- 6-aza-15-oxabicyclo[10.2.1]pentadec-14-en-7-one; and

[2R-(2R*,3R*,4R*,5R*,8R*,9S*,10S*,11R*,12R*)]-9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(i-butylmethylamino)-β-D-xylo-hexopyranosyl]oxy]-6-aza- 15-oxabicyclo[10.2.1]pentadec-14-en-7-one as well as pharmaceutically acceptable salts thereof.

The following terms are used as defined below throughout this disclosure and in the appended claims:

The term "carboxylate" as used herein refers to the anion of an organic carboxylic acid such as acetic, succinic, citric, lactic, maleic, fumaric, palmitic, cholic, pamoic, music, D-glutamic, d-camphoric, glutaric, glycolic, phthalic, tartaric, formic, lauric, stearic, salicylic, methanesulfonic, benzenesulfonic, sorbic, picric, benzoic, cinnamic and like acids.

The term "cyano-substituted loweralkyl" as used herein refers to a loweralkyl group as defined below which has one hydrogen atom replaced by a cyano substituent, as for example cyanomethyl or cyanoethyl.

The term "halogen" refers to chloro (Cl), bromo (Br), fluoro (F) and iodo (I).

The term "halo-substituted loweralkyl" refers to a loweralkyl group as defined below which has one, two or three halogen substituents, as for example fluoroethyl, difluoroethyl, chloromethyl, trifluoroethyl and the like.

The term "hydroxy-substituted loweralkyl" refers to a loweralkyl group as defined below which has one hydrogen atom replaced by a hydroxy substituent, as for example hydroxymethyl or hydroxyethyl.

The term "loweralkanoyl" refers to a substituent of formula $R^{10}C(O)$—wherein $R^{10}$ is hydrogen or a loweralkyl group as defined below.

The term "loweralkenyl" refers to straight or branched chain hydrocarbon groups containing from two to six carbon atoms and possessing at least one carbon-carbon double bond. Examples of loweralkenyl groups include vinyl, allyl, 2- or 3-butenyl,2-,3- or 4-pentenyl and isomeric forms thereof. The double bond(s) can be in either the cis or the trans configuration.

The term "loweralkyl" refers to branched or straight chain alkyl groups comprising one to six carbon atoms including, but not limited to, methyl, ethyl, propyl, isopropyl, n-butyl, isobutyl, t-butyl, neopentyl and the like.

The term "loweralkynyl" refers to hydrocarbon groups containing from two to six carbon atoms and possessing at least one carbon-carbon triple bond. Examples of loweralkynyl groups include ethynyl, propargyl and butynyl.

The term "lowercycloalkyl" refers to cyclic hydrocarbons having three to six ring carbon atoms.

The term "delayed gastric emptying" as used herein refers to a slow evacuation of gastric contents into the small intestine not caused by mechanical obstruction of the gastric outlet. Patients with severe gastric motor dysfunction may be incapacitated from intractable nausea, vomiting and gastric stasis. This may lead to failure to thrive in a young patient or to significant weight loss and malnutrition in adults. (cf. "Medicine for the Practicing Physician Second Edition", ed. J. Willis Hurst, Butterworth Publishers, Boston, 1988, pages 1364–66.

The term "gastroparesis" refers to paralysis of the stomach.

The term "intestinal pseudoobstruction" refers to a condition characterized by constipation, colicky pain and vomiting, but without evidence of organic obstruction apparent at laparotomy (abdominal surgery).

The term "paralytic or adynamic ileus" refers to obstruction of the intestines resulting from inhibition of bowel motility.

The term "reflux esophagitis" refers to inflammation of the esophagus as a result of frequent or chronic backward or return flow of stomach contents into the esophagus.

By "pharmaceutically acceptable salts" is meant those acid addition salts of the compounds of formula (I) which are, within the scope of sound medical judgement, suitable for use in contact with the tissues of humans and lower animals without undue toxicity, irritation, allergic response, and the like commensurate with a reasonable benefit/risk ratio, and which are effective for their intended use.

Pharmaceutically acceptable salts are well known in the art. For example, S. M Berge et al. describe pharmaceutically salts in detail in *J. Pharmaceutical Sciences*, 1977, vol. 66, pages 1–19. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include nitrate, bisulfate, borate, formate, butyrate, valerate, 3-phenylpropionate, camphorate, adipate, benzoate, oleate, palmitate, stearate, laurate, lactate, fumarate, ascorbate, aspartate, nicotinate, p-toluenesulfonate, camphorsulfonate, methanesulfonate, 2-hydroxyethanesulfonate, gluconate, glucoheptonate, lactobionate, glycerophosphate, pectinate, lauryl sulfate, alginate, cyclopentanepropionate, digluconate, dodecylsulfate, ethanesulfonate, hemisulfate, heptonate, hexanoate, 2-naphthalenesulfonate, pamoate, persulfate, pivalate, propionate, undecanoate salts and the like, and may be prepared according to conventional methods. Representative alkali or alkaline earth metal salts include sodium, calcium, potassium, magnesium salts and the like. Pharmaceutically acceptable countedons for the quaternary ammonium salt compounds formed when $R^3$ is present include halide, hydroxide, carboxylate, sulfate, phosphate, nitrate, loweralkyl sulfonate and arysulfonate.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringers solution; ethyl alcohol, and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator.

By a "therapeutically effective amount" of a compound of the invention is meant a sufficient amount of the compound to treat a gastrointestinal disorder, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, of from about 0.01 to about 25 mg/kg body weight or, more usually, from about 0.1 to about 15 mg/kg body weight. Single dose compositions may contain such amounts or submultiples thereof as make up the daily dose. In general, treatment regimens according to the present invention comprise administration to a patient in need of such treatment of from about 10 mg to about 1000 mg of the compound(s) of this invention per day in multiple doses or in a single dose.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants such as wetting agents; emulsifying or suspending agents and sweetening, flavoring or perfuming agents.

Injectable preparations, as for example sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, as for example in solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid may be used in the preparation of injectables.

The injectable formulation can be sterilized, as for example by filtration through a bacteria-retaining filter or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, as for example, its crystal size and crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such exipients as lactose or milk sugar as well as high molecular weight polyethylene glycols and the like.

The active compounds can also be combined in microencapsulated form with one or more excipients as noted above. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

The compounds of the present invention may be synthesized by the reaction schemes I through VII presented below, in which A and $R^1$-$R^9$ correspond to the groups defined with respect to formula (I). However, it should be noted that, prior to ring closure and formation of a lactam, $R^6$ in the following schemes is limited to hydrogen and —OH. Moreover, it will be observed that certain schemes, such as Scheme IA, are useful only where $R^6$ is —OH.

Scheme I

Erythromycin A or C is treated with a suitable reagent for acetylating the 2'-hydroxyl group, such as acetic anhydride or acetyl chloride, in the presence of a suitable base, such as triethylamine, pyridine or DMAP. The resulting 2'-O-acetyl compound is converted to a ring-contracted compound of Formula 3 by treatment with an appropriate nonaqueous acid, such as glacial acetic acid followed by treatment with a suitable base, preferably in a polar solvent, as for example treatment with potassium carbonate in DMF or ammonium acetate in methanol. Alternatively, compounds of Formula I are converted directly into the compounds of Formula 3 by the procedure described in Scheme 1A below.

The compound of Formula 3 is, in turn, converted to the epoxide of Formula 4 by treatment with bis[a,a-bis(trifluoromethyl)benzene-methanolato]-diphenyl sulfur (Martin sulfurane). Alternately the hydroxy group on carbon number 13 is activated by treatment with a suitable reagent, as for example methanesulfonyl chloride, and the activated ester is displaced to form an epoxide upon treatment with a suitable base, as for example sodium or potassium hydroxide or sodium or potassium methoxide or t-butoxide, sodium or potassium carbonate. The epoxide ring of the compound of Formula 4 is then opened to form an azido alcohol of Formula 5 by treatment with a nucleophilic hydrozoic acid derivative, such as sodium azide or potassium azide. The azido alcohol is, in turn, converted to an amino alcohol of Formula 10 by treatment with a suitable reducing agent, as for example by hydrogenation in the presence of a catalyst such as Raney nickel, palladium on carbon or platinum oxide, treatment with zinc in acetic acid, or treatment with lithium aluminum hydride. The amino alcohol is cyclized to form a lactam of Formula IA by treatment with a suitable base in a suitable solvent such as ammonium hydroxide in methanol or 1,8-diazabicyclo[5.4.0]undec-7-ene (DBU) in toluene.

Scheme IA

According to scheme IA, which is the preferred scheme for the synthesis of compounds of Formula 11, the compounds of Formula 1 are reacted in a two-part procedure to convert them into compounds of Formula 3. The compound of Formula 1 is first treated with a strong organic acid, as for example acetic acid, dichloroacetic acid, difluoroacetic acid, trichloroacetic acid or glycolic acid in a polar organic solvent such as methanol, DMF or acetonitrile. The reaction intermediate is not isolated, but treated directly with a suitable base such as ammonium acetate or potassium carbonate in a suitable organic solvent, such as methanol, DMF or acetonitrile, to form the compound of Formula 3. Preferred reagents are dichloroacetic acid in acetonitrile, followed by potassium carbonate in an aqueous mixture of acetonitrile and methanol. The compounds of Formula 3 are then converted to epoxides of Formula 4 by the methods described above in reaction scheme I. These epoxides are subsequently treated with an amine, as for example ammonia or methylamine and preferably in a polar solvent, to afford the compounds of Formula 11. More preferably, the compounds of Formula 4 are treated with a methanolic solution of the appropriate amine.

Scheme II

2'-O-Acetyl erythromycin (A, B, C or D) is treated with a suitable reagent for protecting the 4"-hydroxyl group, such as benzyloxycarbonyl chloride, in the presence of a suitable base, such as dimethylaminopyridine. The reaction is carried out in an inert solvent such as methylene chloride and preferably at a low temperature, more preferably at $-25°$ C., to afford a 2'-O-acetyl-4"-O-benzyloxycarbonyl erythromycin derivative. This compound is optionally treated with methanol to remove the acetyl group and is treated sequentially with a suitable nonaqueous acid, such as glacial acetic acid, and a suitable base, such as potassium carbonate in DMF or ammonium acetate in methanol, to afford a compound of Formula 6. A compound of Formula 6 is optionally treated with a suitable reagent for reacetylating the 2'-hydroxyl group and is treated with a suitable oxidizing agent such as N-chlorosuccinimide/dimethyl sulfide/triethylamine or tetrapropylammonium perruthenate/N-methylmorpholine N-oxide to give a ketone of Formula 7. If the acetyl group is present it is removed with methanol, and the protecting group on the 4"-hydroxyl group is removed (preferably by hydrogenolysis, if the protecting group is CBZ) to give a compound of Formula 8.

The ketone of Formula 8 is converted to an oxime of Formula 9 by treatment with hydroxylamine in the presence of a suitable base such as triethylamine. The oxime of Formula 9 is reduced under suitable conditions, as for example 4 atmospheres of hydrogen over a catalyst such as Raney nickel to afford a mixture of stereoisomers of the amino compounds of Formula 10 (in which the amino bond is shown as a wavy line to represent both steric orientations). One isomer of the amino compound is cyclized to a lactam of Formula 11 by treatment with a suitable base in an appropriate solvent, as for example ammonium hydroxide in methanol or DBU in toluene.

Scheme III

According to reaction scheme III, an erythromycin lactam of Formula 11 is treated with iodine and light in the presence of a suitable base, such as sodium acetate, to afford a N-demethyl derivative of Formula 12. A compound of Formula 12 is, in turn, treated with a suitable alkylating agent such as allyl bromide to afford a compound of Formula 13. Alternatively, a compound of Formula 12 is treated with an appropriate aldehyde to give an imine which is reduced (preferably in situ) by hydrogenation in the presence of a suitable catalyst as for example, palladium on carbon, to afford a compound of Formula 13. The compounds of Formula 13 are treated with iodine and light in the presence of a suitable base, for example sodium acetate, to afford the N-demethyl derivative of Formula 14. A compound of Formula 14 is, in turn, treated with a suitable alkylating agent such as allyl bromide to afford a compound of Formula 15. Alternatively, a compound of Formula 14 is treated with an appropriate aldehyde, as for example acetaldehyde, to give an imine which is reduced (preferably in situ) by hydrogenation in the presence of a suitable catalyst, as for example palladium on carbon, to afford a compound of Formula 15.

Other alkylating agents which may be used in preparing compounds of Formula 13 and Formula 15 are loweralkyl halides such as ethyl bromide, halo-substituted loweralkyl halides, cyano-substituted loweralkyl halides, hydroxy-substituted loweralkyl halides, other loweralkenyl halides such as methylallyl chloride, loweralkynyl halides such as propargyl bromide, lower cycloalkyl halides, lower cycloalkylmethyl halides such as lower cyclopropylmethyl and benzyl halides.

Scheme IV

According to reaction scheme IV, an erythromycin lactam derivative of Formula 11 or 15 is treated with an a loweralkyl halide such as methyl iodide or ethyl bromide, a loweralkenyl halide such as allyl bromide, a loweralkynyl halide such as propargyl bromide or a benzyl halide such as benzyl bromide to afford a quaternary salt derivative of Formula 16.

Scheme V

According to reaction scheme V, an erythromycin A or C lactam of Formula 11 or 15 (wherein $R^5$ and $R^6$ are both OH) is treated with a suitable carbonic acid derivative such as ethylene carbonate, carbonyl diimidazole or thiocarbonyl diimidazole to afford a carbonate derivative of Formula 17. Methods for preparing the loweralkanoyl and $—S(O)_2CH_3$ derivatives (compounds of formula (I) wherein $R^5$ or $R^6$ are loweralkanoyl and $—S(O)_2CH_3$) are well known in the art are, for example, are described by S. Omura and Z. Itoh in European Application Number 213,617, published Nov. 3, 1987. Alternatively, reaction of a suitably protected lactam of formula 11 or 15 with a base, for example, sodium hydride, and an alkylating agent, such as methyl iodide, affords alkyl derivatives wherein R5 or R6 may be a loweralkyl group.

Scheme VI

According to reaction scheme VI, an erythromycin lactam of Formula 11 is reduced by catalytic hydrogenation using a suitable catalyst such as platinum oxide in the presence of a suitable acid such as difluoroacetic acid in a suitable solvent, preferably acetic acid, to afford the compounds of Formula 18.

Scheme VII

According to reaction scheme VII, an erythromycin lactam of Formula 11 (wherein $R^6$ is OH) is treated with aqueous acid to afford a mixture of compounds which includes the compounds of Formulas 19 and 20. The compounds of Formulas 19 and 20 (wherein wavy lines indicate both stereoisomers are formed) are also formed in vivo when compounds of Formula 11 are exposed to the acidic conditions of the stomach.

Scheme VIII

According to Scheme VIII, the ring-contracted epoxide compound of Formula 4 is treated with a suitable reagent for acetylating the 2'-hydroxyl group, such as acetic anhydride or acetyl chloride, in the presence of a suitable base, such as triethylamine, pyridine or DMAP. The compound of Formula 21 is converted to the 4"-deoxy compound by treatment with 1,1'-thiocarbonyldiimidazole (Aldrich Chemical Co., Milwaukee, Wis.) in the presence of a suitable base such as triethylamine, pyridine or DMAP. The compound of Formula 21 is in turn treated with a selective reducing agent, as for example tri-n-butyl tin hydride and AIBN (2,2'-azobis(2-methylpropionitrile), Alfa Catalog Chemicals) in an inert atmosphere to give the 4"-deoxy compound of Formula 23. This compound is then treated with an appropriate amine, such as ammonia or methylamine, and preferably in a polar solvent, to afford the desired 4"-deoxy lactams (compounds 24 and 25). These compounds may optionally be further modified by the reactions described in the previous Schemes III–VII, substituting the compounds of Formula 24 or 25 for compounds of Formula 11.

Scheme 1

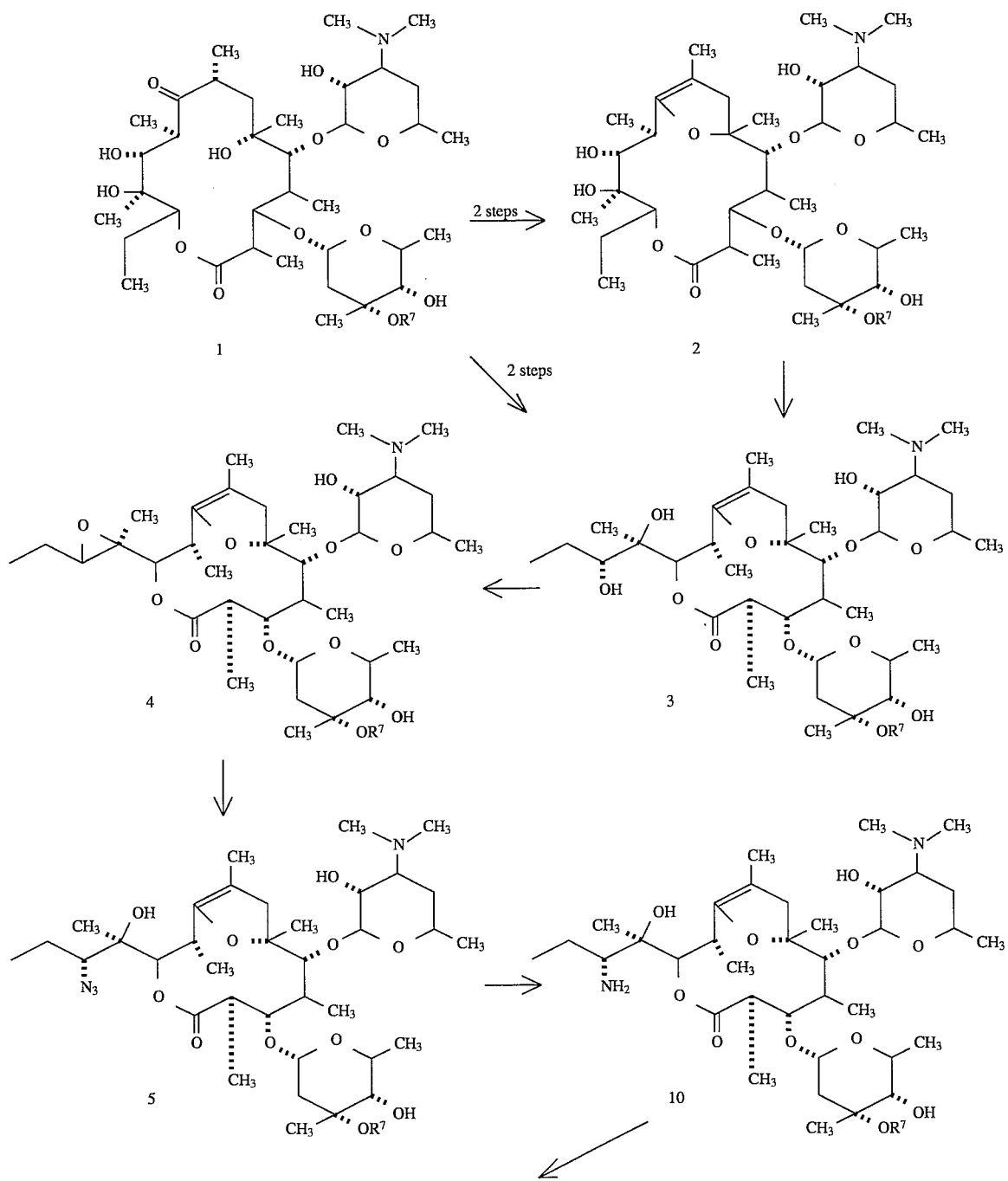

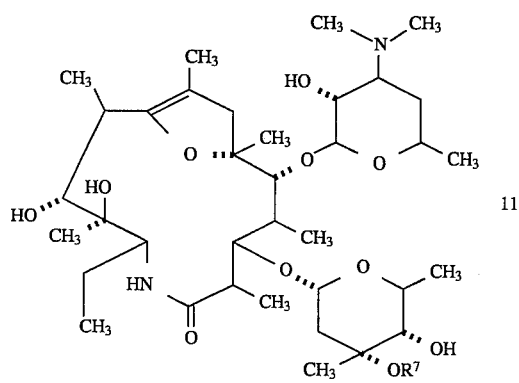
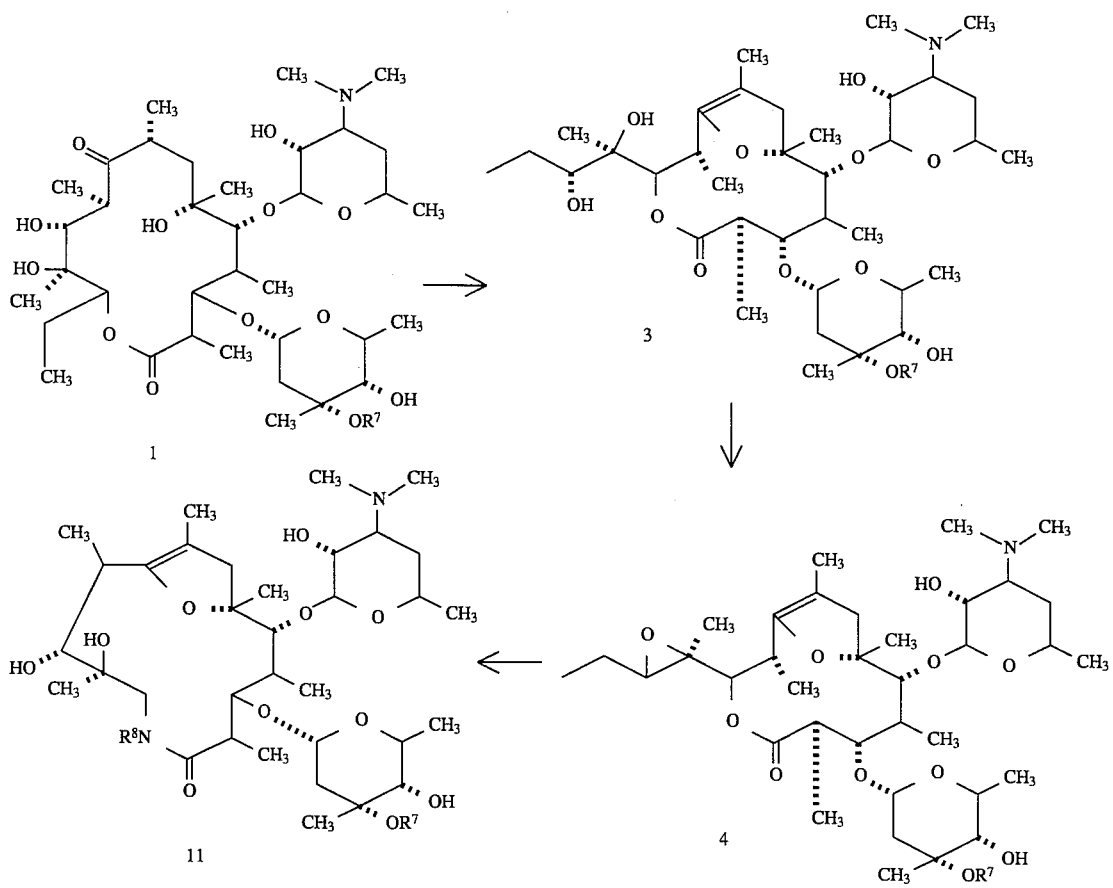
Scheme IA

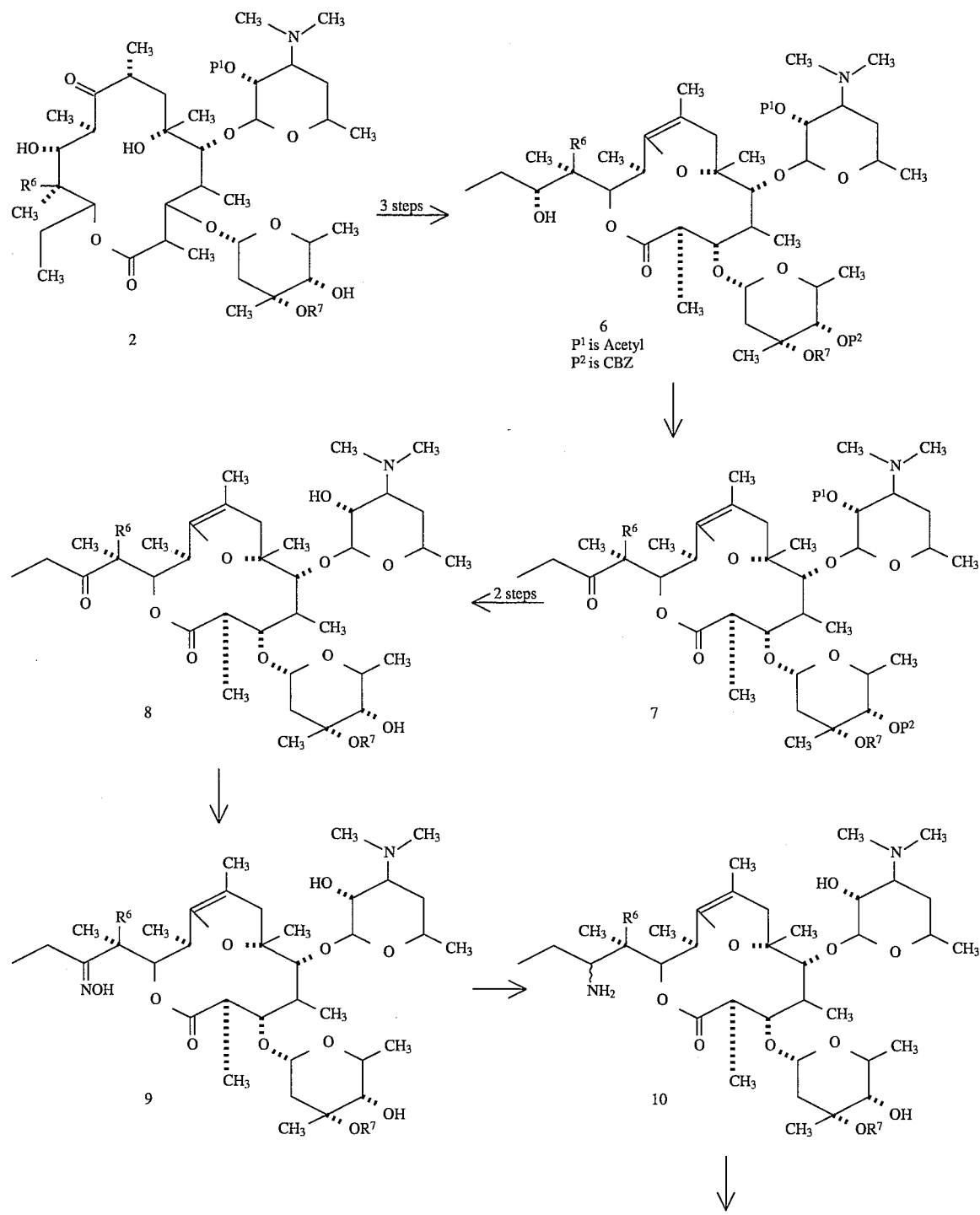
Scheme II

-continued
Scheme II
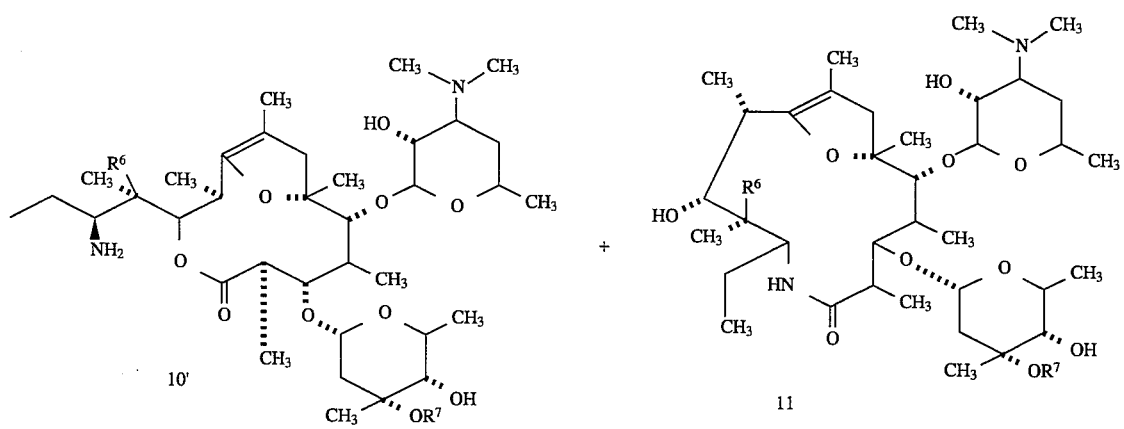
Scheme III
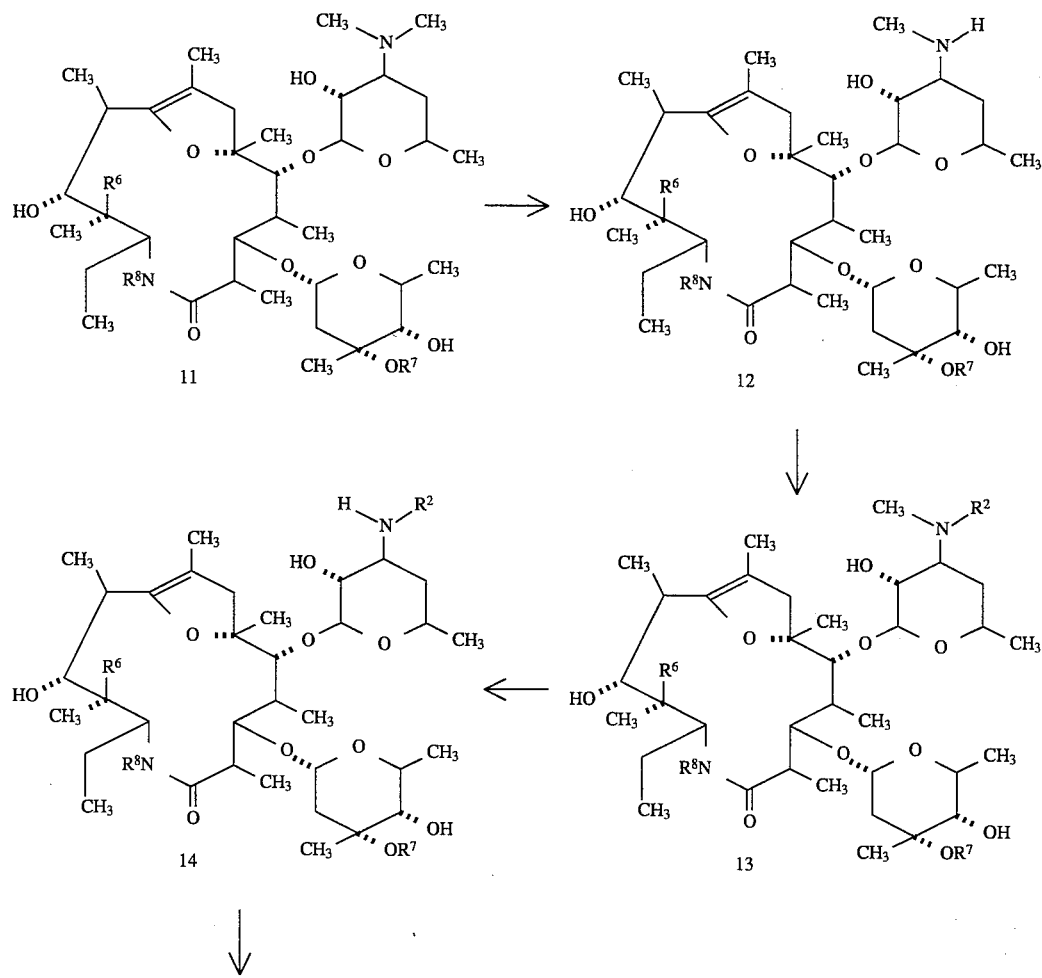

-continued
Scheme III
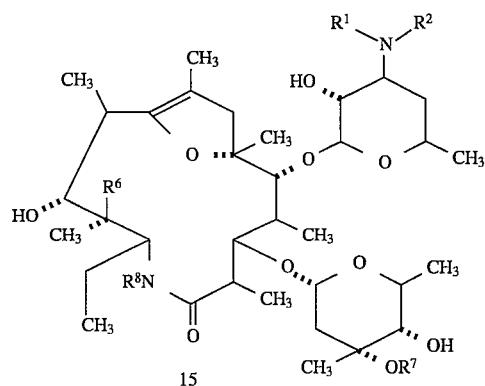
15
Scheme IV
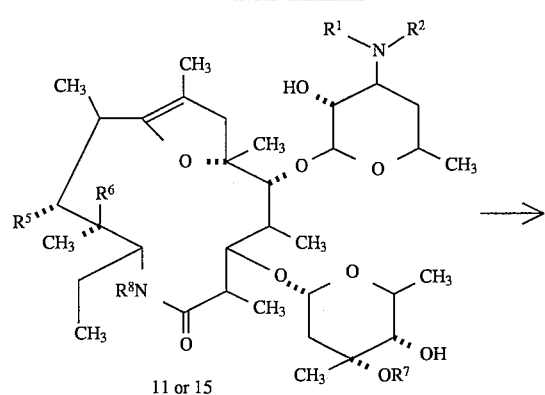
11 or 15
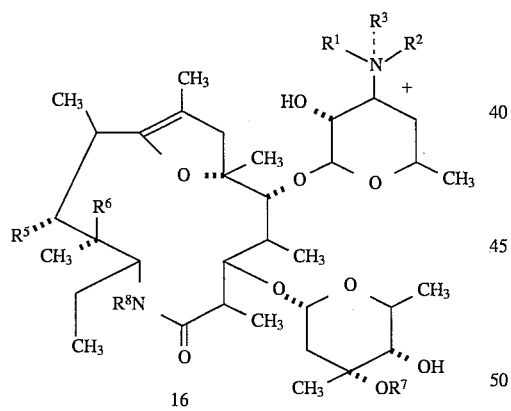
16
Scheme V
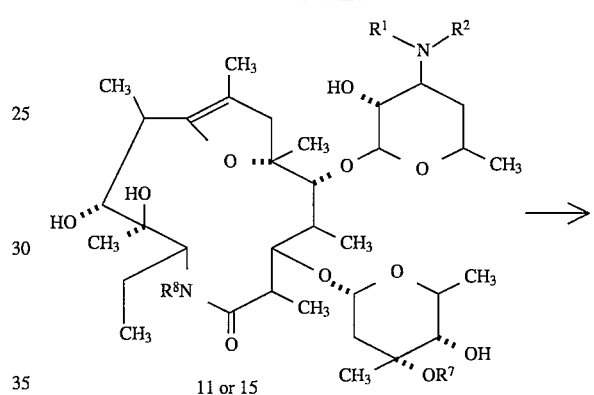
11 or 15
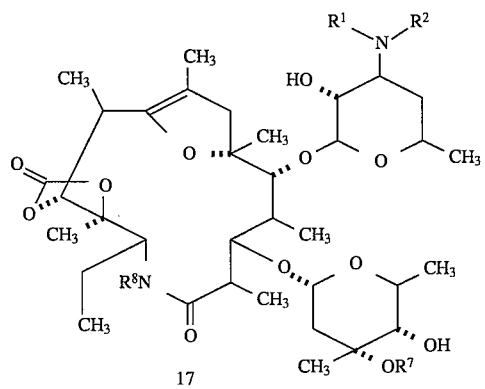
17

Scheme VI
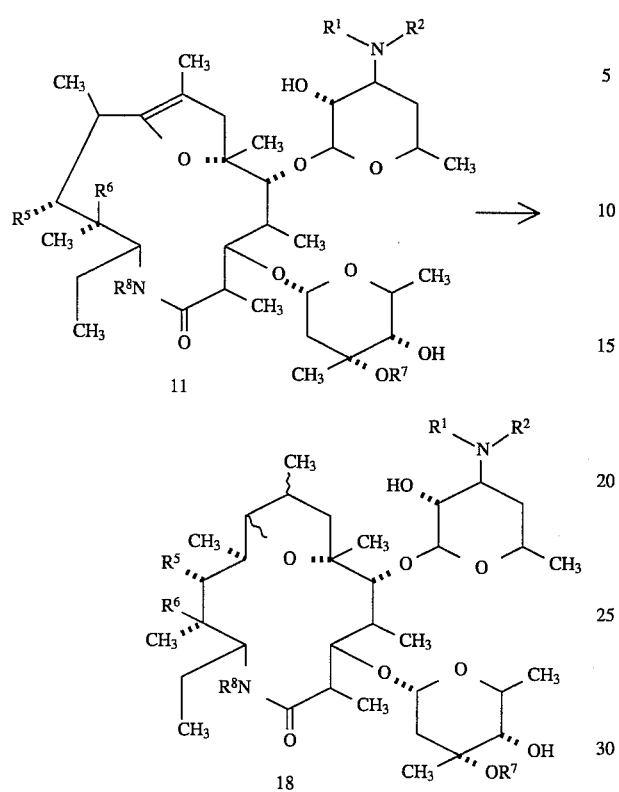
Scheme VII
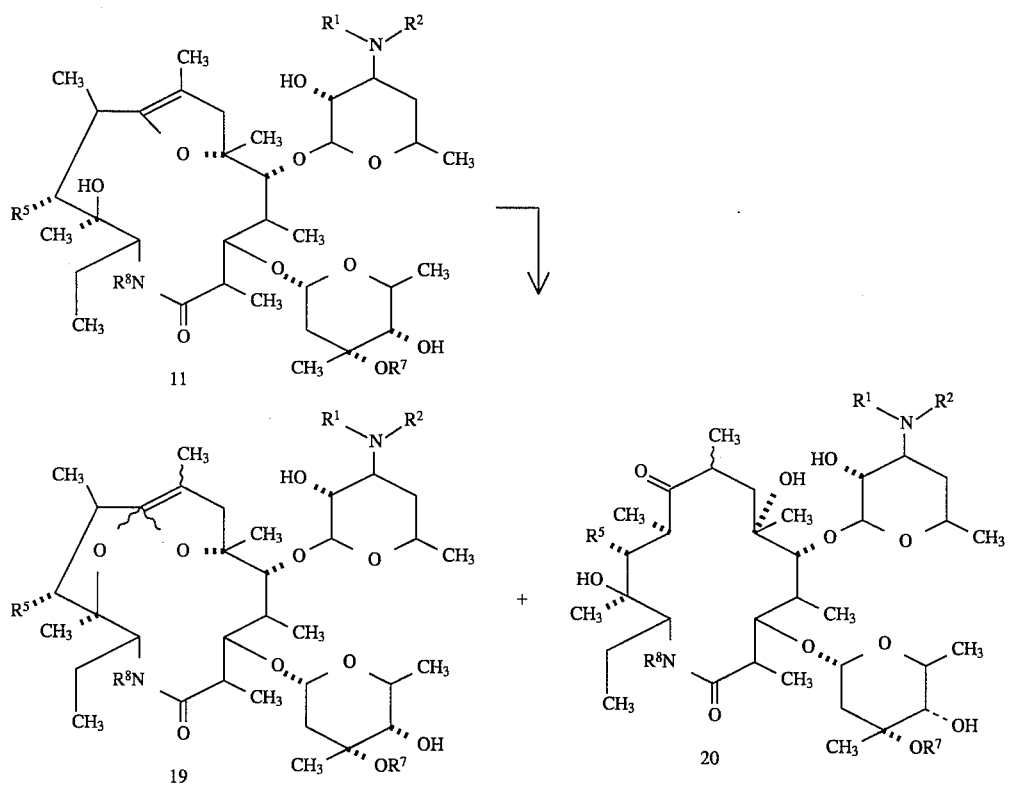

Scheme VIII
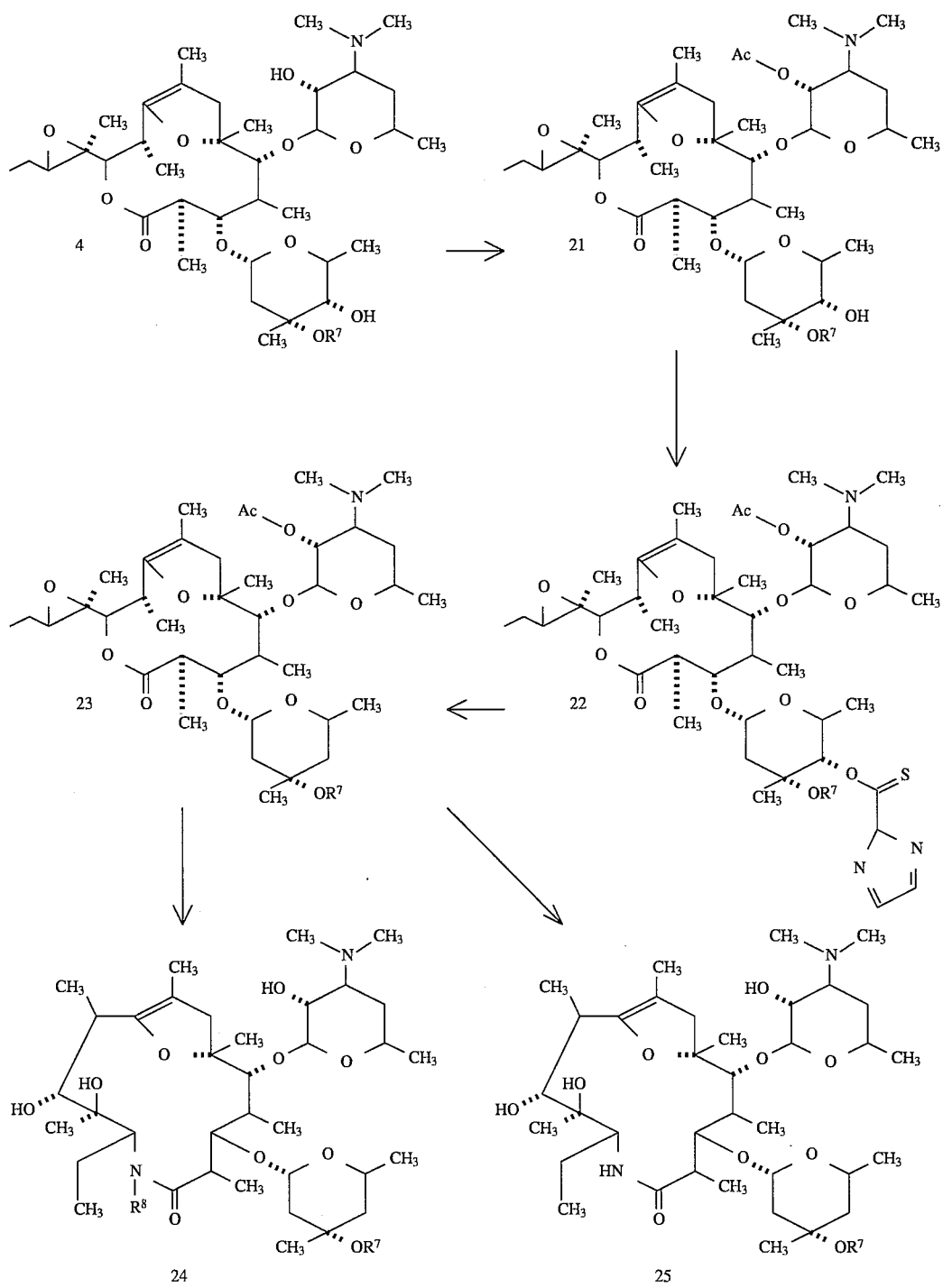
The foregoing may be better understood by reference to the following examples, which are provided for illustration only and are not intended as a limitation of the invention.

EXAMPLE 1

[2R-(2R*,3R*,4R*,5R*,8R*,9S*,
10S*,11R*,12R*)]-9-[
(2,6-Dideoxy-3-C-methyl-3-C-methyl-3-O-
methyl-α-L-ribo-hexopyranosyl)oxy]-
5-ethyl-3,4-dihydroxy-2,4,8,10,12,14-hexamethyl-
11-[[3,4,6-trideoxy-3-(dimethylamino)-β-
D-xylo-hexopyranosyl]oxy]-
6-aza-15-oxabicyclo[10.2.1]pentadec-14-en-7-one Step 1: 2'-O-Acetylerythromycin A Erythromycin A (50.0 g, 68.1 mmol) (commercially available from Abbott Laboratories) was dissolved in 600 mL of methylene chloride (CH₂Cl₂) at ambient temperature. Triethylamine (20 mL) and 10 mL (10.82 g, 106 mmol) of acetic anhydride were added to this solution. The reaction mixture was heated to reflux and 100 mL of CH₂Cl₂ was distilled from the reaction mixture to remove any traces of water. The reaction mixture was heated at reflux temperature for an additional five hours. After six hours, when the reaction was complete, according to TLC analysis, the reaction mixture was cooled to ambient temperature and transferred to a separatory funnel. The CH₂Cl₂ solution was washed with 300 mL of ammonium hydroxide/sodium bicarbonate solution containing 2.9% ammonia and 1.8% sodium bicarbonate, dried over anhydrous sodium sulfate and filtered. The CH₂Cl₂ was removed using a rotary evaporator with a water bath temperature of 30°–40° C. The residue was crystallized from 200 mL of acetonitrile (CH₃CN) by first dissolving it in hot CH₃CN and allowing the solution to stand overnight at ambient temperature, then cooling it to –25° C. and maintaining this temperature for 24 hours. The product was isolated as white crystals which were washed with cold (–25° C.) CH₃CN and dried in a vacuum oven at 50° C. for approximately 64 hours. The 2'-O-acetylerythromycin A was obtained in 83% yield (43.91 g).

Step 2: 2'-O-Acetyl-8,9-didehydro-9-deoxo-6-deoxy-6,9-epoxyerythromycin A

2'-O-Acetylerythromycin A (20 g, 25.8 mmol) from Step 1 was dissolved in 115 mL of glacial acetic acid. The resultant solution was stirred at ambient temperature for 2 hours. The acetic acid was removed in vacuo. The complete removal of the acetic acid was accomplished by azeotropic distillation with toluene. The residue was dissolved in 200 mL of ethyl acetate and was washed with a mixture of 100 mL of 5% aqueous sodium bicarbonate solution and 10 mL of concentrated aqueous ammonium hydroxide solution. The aqueous layer was extracted with 3×100 mL of ethyl acetate. The combined ethyl acetate layers were washed with 200 mL of brine, dried over anhydrous sodium sulfate, filtered and concentrated in vacuo. The residue (19.67 g) was crystallized from ethyl acetate to give 13.54 g (69% yield) of the title compound: DCI-NH₃ MS M/Z: 758 (M+H)⁺.

Step 3: [2R-[2R*,3R*(1R*,2R*),6R *,7S*,8S*,9R*, 10R*]
]-7-[(2,6-Dideoxy-3-C-methyl-3-O-methyl-α-L-ribo-hexopyranosyl)oxy]- 3-(1,2-dihydroxy-1-methylbutyl)-2,6,8,10,12-pentamethyl-9-[[3,4,6-trideoxy-3-(dimethylamino)-β-D-xylo-hexopyranosyl]oxy]-4,13-dioxabicyclo[8.2.1]tridec-12-en-5-one 2'O-Acetyl-8,9-didehydro-9-deoxo-6-deoxy-6,9-epoxyerythromycin A (5.75 g, 7.6 mmol) from Step 1 was dissolved in 35 mL of anhydrous N,N-dimethylformamide (DMF). Solid anhydrous potassium carbonate was finely powdered and added to the resultant solution. The suspension was stirred at ambient temperature for 3 days. The reaction mixture was diluted with ice-water (100 mL) and was extracted with ethyl acetate (1×150 mL and 3×50 mL). The combined ethyl acetate layers were washed with 100 mL of brine, dried over anhydrous sodium sulfate, filtered and concentrated in vacuo. The residue (7.03 g) was chromatographed on 150 g of silica gel eluted with toluene:methanol (10:1). The residue was dissolved in methanol and the solution was left overnight at ambient temperature to cleave the acetyl group. The solution was concentrated in vacuo to give 1.56 g (29% yield) of the title compound; IR (0.15% in CCl4) 3600, 3550 and 1720 cm⁻¹.

Step 4: [2R-[2R*,3R*(1R*,2S*),6R*,7S*,8S*,9R*,10R*]]-7-[(2,6-Dideoxy-3-C-methyl- 3-O-methyl-α-L-ribo-hexopyranosyl)oxy]-3-(1,2-epoxy-1-methylbutyl)-2,6,8,10,12-pentamethyl- 9-[[3,4,6-trideoxy-3-(dimethylamino)-β-D-xylo-hexopyranosyl]oxy]- 4,13-dioxabicyclo[8.2.1 ]tridec-12-en-5-one

[2R-[2R*,3R*(1R*,2R*),6R*,7S*,8S*,9R*, 10R*]]-7-[(2,6-Dideoxy-3-C-methyl-3-O-methyl-α-L- ribo-hexopyranosyl)oxy]- 3-(1,2-dihydroxy-1-methylbutyl)-2,6,8,10,12-pentamethyl- 9-[[3,4,6-trideoxy-3-(dimethylamino)-β-D-xylo-hexopyranosyl]oxy]4,13-dioxabicyclo [8.2.1]tridec-12-en-5-one (0.5 g, 0.7 mmol) from Step 3 was dissolved in 1 mL of dry methylene chloride and the resultant solution was added dropwise to a stirred solution of 0.94 g (1.4 mmol) of stirred bis[a,a-bis(trifluoromethyl)benzene-methanolato]-diphenylsulfur (Martin sulfurane; commercially available from Aldrich Chemical Company) in 1 mL of dry methylene chloride. The reaction mixture was stirred for 45 minutes and then poured into a separatory funnel containing 30 mL of ethyl acetate. Aqueous 5% sodium bicarbonate solution (30 mL) was added until the pH of the solution was neutral. The ethyl acetate layer was separated and the aqueous mixture was extracted with 3×10 mL of ethyl acetate. The combined ethyl acetate layers were washed with brine, dried over anhydrous sodium sulfate, filtered and concentrated in vacuo to a yellow oil. The residue was chromatographed on approximately 50 g of silica gel eluted sequentially with 2 L of toluene/acetone (5:1), 2,125 mL of toluene/methanol (10:1) and 1500 mL of toluene/methanol (5:2) to give 0.5 g of the title compound; DCI NH₃ MS M/Z: 698 (M+H)⁺; IR (0.15% in CCl₄) 3555 and 1725 cm⁻¹.

Step 5: [2R-[2R*,3R*(1R*,2R*),6R*,7S*,8S*,9R*, 10R*]] 3-(2-Azido-1-hydroxy-1-methylbutyl)- 7-[(2,6-dideoxy-3-C-methyl-3-O-methyl-α-L-ribo-hexopyranosyl)oxy]-2,6,8,10,12-pentamethyl-9-[[3,4,6-trideoxy-3-(dimethylamino)-β-D-xylo-hexopyranosyl]oxy]-4,13-dioxabicyclo[8.2.1 ]tridec-12-en-5-one

[2R-[2R*,3R*(1R*,2S*), 6R*,7S*,8S*,9R*, 10R*]]-7-[(2,6-Dideoxy-3-C-methyl-3-O-methyl-α-L- ribo-hexopyranosyl)oxy]- 3-(1,2-epoxy-1-methylbutyl)-2,6,8,10,12pentamethyl- 9-[[3,4,6-trideoxy-3-(dimethylamino)-β-D-xylo-hexopyranosyl]oxy]4,13-dioxabicyclo[8.2.1 ]tridec-12-en-5-one (14.19 g, 20.3 mmol), from Step 4, was dissolved in 350 mL of 2-methoxyethanol. To this solution, with stirring, was added a solution of 10.6 g (0.163 mmol) of sodium azide and 0.853 g (0.16 mmol) of ammonium chloride in 141 mL of water. The reaction mixture was heated at reflux temperature for 5 days. The reaction mixture was transferred to a separatory funnel and 200 mL of 5% aqueous sodium bicarbonate was added. The mixture was extracted with 200 mL of methylene chloride followed by 2×100 mL of methylene chloride. The combined organic layers were washed with brine, dried over anhydrous sodium sulfate, filtered and concentrated in vacuo to a yellow oil. The oil was chromatographed on approximately 500 g of silica gel eluted with chloroform/methanol/ammonia (10:1:

0.0125) to give 8.5 g (57% yield) of the title compound as a yellow glass; DCI NH₃ MS M/Z: 741 (M+H)⁺; IR (0.15% in CCl₄) 3590, 3548, 3470, 2110 and 1735 cm⁻¹.

Step 6: [2R-[2R*,3R*(1R*,2R*),6R*, 7S*,8S*,9R*,10R*]]-3-(2-Amino-1-hydroxy-1-methylbutyl)- 7-[(2,6-dideoxy-3-C-methyl-3-O-methyl-α-L-ribo-hexopyranosyl)oxy]-2,6,8, 10,12-pentamethyl-9-[[3,4,6-trideoxy-3-(dimethylamino)-β-D-xylo-hexopyranosyl]oxy]-4,13-dioxabicyclo[8.2.1]tridec-12-en-5-one

[2R-[2R*,3R*(1R*,2R*), 6R*,7S*,8S*,9R*, 10R*]]-3-(2-Azido-1-hydroxy-1-methylbutyl)- 7-[(2,6-dideoxy-3-C-methyl-3-O-methyl-α-L- ribo-hexopyranosyl)oxy]- 2,6,8,10,12-pentamethyl-9-[[3,4,6-trideoxy-3-(dimethylamino)-β-D-xylo-hexopyranosyl]oxy]-4,13-dioxabicyclo[8.2.1]tridec-12-en-5-one (1 g, 1.35 mmol) from Step 5, 4.5 g of Raney nickel and 100 mL of methanol were combined under 4 atmospheres of hydrogen and the mixture was shaken at ambient temperature for 24 hours. The catalyst was removed by filtration and the filtrate concentrated under reduced pressure to a light-green glass. The glass (1.08 g) was dissolved in 100 mL of methylene chloride and washed with 100 mL of 5% aqueous sodium bicarbonate. The aqueous layer was extracted with 3×50 mL of methylene chloride. The combined organic layers were washed with brine, dried over anhydrous sodium sulfate, filtered and concentrated in vacuo to 880 mg (91% yield) of the title compound; DCI NH₃ MS M/Z: 715 (M+H)⁺; IR (0.15% in CCl₄) 3595, 3548, 3470, and 1725 cm⁻¹. Analysis calculated for $C_{37}H_{66}N_2O_{11}$: C, 2.16; H, 9.31; N, 3.92. Found: C, 62.19; H, 9.21; N, 3.52.

Step 7: [2R-(2R*,3R*,4R*,5R*,8R*,9S*,10S*,11R*,12R*)]-2,6-Dideoxy-3-C-methyl- 3-O-methyl-α-L-ribo-hexopyranosyl)oxy]-5-ethyl-3,4-dihydroxy- 2,4,8,10,12,14-hexamethyl-11-[[3,4,6-trideoxy-3-(di-methylamino)-β-D-xylo-hexopyranosyl]oxy]- 6-aza-15-oxabicyclo [10.2.1]pentadec-14-en-7-one

[2R-[2R*,3R*(1R*,2R*), 6R*,7S*,8S*,9R*, 10R*]]-3-(2-Amino-1-hydroxy-1-methylbutyl)- 7-[(2,6-dideoxy-3-C-methyl-3-O-methyl-α-L-ribo-hexopyranosyl)oxy]-2,6,8,10,12-pentamethyl-9-[[3,4,6-trideoxy- 3-(dimethylamino)-β-D-xylo-hexopyranosyl]oxy]-4,13-dioxabicyclo[8.2.1]tridec-12-en-5-one (0.81 g, 1.1 mmol) was dissolved in 88 mL of methanol. Ammonium hydroxide (8.5 mL) was added and the reaction mixture was stirred at ambient temperature for 24 hours. The solvent was removed in vacuo. Methylene chloride was added to and evaporated from the residue twice to remove residual water affording 770 mg (95% yield) of the title compound; DCI NH₃ MS M/Z: 715 (M+H)⁺; IR (0.15% in CCl₄) 3560, 3442, 3358, 1703 and 1660 cm⁻¹.

EXAMPLE 1 A

Alternate preparation of

[2R-(2R*,3R*,4R*,5R*,8R*,9S*,10S*,11R*,12R*)]-9-[( 2.6-Dideoxy-3-C-methyl-3-O-methyl-α-L-ribo-hexopyranosyl)oxy]-5-ethyl-3.4-dihydroxy-2,4,8,10,12,14,hexamethyl-11-[[3,4,6-trideoxy-3-(dimethylamino)-β-D-xylo-hexopyranosyl]oxy]-6-aza-15-oxabicyclo[10.2.1]pentadec-14-en-7-one Step 1: [2R-[2R*,3R*(1R*,2R*),6R*,7S*,8S*,9R*,10R*]]- 7-[(2,6-Dideoxy-3-C-methyl- 3-O-methyl-α-L-ribo-hexopyranosyl)oxy]-3-(1,2-dihydroxy-1-methylbutyl)-2,6,8,10,12-pentamethyl-9-[[3,4,6-trideoxy-3-(dimethylamino)-β-D-xylo-hexopyranosyl]oxy]-4,13-dioxabicyclo]8.2.1]tridec-12-en-5-one (the product of Step 3 of Example 1)

Erythromycin A (100 g, 136.25 mmol) was dissolved in 1 L of methanol and 62.5 mL (1090 mmol, 8 equivalents) of glacial acetic acid was added. The reaction mixture was heated to reflux and refluxed for 4.25 hours. The reaction mixture was then cooled in an ice bath and to the cooled mixture was added, dropwise over a 15 minute period, 73.5 mL (1090 mmol, 8 equivalents) of concentrated ammonium hydroxide. The reaction mixture was then brought to reflux and refluxed for 24 hours. After keeping the reaction mixture at 25° C. overnight, it was concentrated to a solid mass under reduced pressure using a water bath at 55° C. The residue was taken up in a mixture of 500 mL of ethyl acetate, 400 mL of water and 100 mL of concentrated ammonium hydroxide. After stirring for approximately 20 min, the ethyl acetate layer was separated and the aqueous layer was extracted with 250 mL of ethyl acetate. The combined ethyl acetate solution was washed with 2×350 mL of brine and 2×350 mL of water, dried over anhydrous sodium sulfate, filtered and concentrated to dryness. The residue was dried at 25° C. (1 mm Hg) for 18 hours to afford 93.1 g of the crude product. The crude product was dissolved in 300 mL of acetonitrile and allowed to crystallize (4 hours at ambient temperature and approximately 65 hours at −25° C.). The crystals were dried at 65° C. (over P₂O₅) in a vacuum oven to give 54.2 g of the title compound, m.p. 125°–130° C.

Step 2: [2R-[2R*,3R*(1R*,2S*),6R*,7S*,8S*,9R*,10R*]]-7-[(2,6-Dideoxy-3-C-methyl- 3-O-methyl-α-L-ribo-hexopyranosyl)oxy]-3-(1,2-epoxy-1-methylbutyl)-2,6,8,10,12-pentamethyl- 9-[[3,4,6-trideoxy-3-(dimethylamino)-β-D-xylo-hexopyranosyl]oxy]-4,13-dioxabicyclo[8.2.1]tridec-12-en-5-one

[2R-[2R*,3R*(1R*,2R*), 6R*,7S*,8S*,9R*, 10R*]]-7-[(2,6Dideoxy-3-C-methyl- 3-O-methyl-α-L-ribo-hexopyranosyl)oxy]- 3-(1,2-dihydroxy-1-methylbutyl)-2,6, 8,10,12-pentamethyl- 9-[[3,4,6-trideoxy-3-(dimethylamino)-β-D-xylo-hexopyranosyl]oxy]-4,13-dioxabicyclo [8.2.1]tridec-12-en-5-one (0.5 g, 0.7 mmol) from Step 1 was dissolved in 1 mL of dry methylene chloride and the resultant solution was added dropwise to a stirred solution of 0.94 g (1.4 mmol) of bis[a,a-bis(trifluoromethyl)benzene-methanolato]-diphenylsulfur (Martin sulfurane; commercially available from Aldrich Chemical Company) in 1 mL of methylene chloride. The reaction mixture was stirred for 45 minutes and then poured into a separatory funnel containing 30 mL of ethyl acetate. Aqueous 5% sodium bicarbonate solution (30 mL) was added until the pH of the solution was neutral. The ethyl acetate layer was separated and the aqueous mixture was extracted with 3×10 mL of ethyl acetate. The combined ethyl acetate layers were washed with brine, dried over anhydrous sodium sulfate, filtered and concentrated in vacuo to a yellow oil. The residue was chromatographed on approximately 50 g of silica gel eluted sequentially with 2 L of toluene/acetone (5:1), 2,125 mL of toluene/methanol (10:1) and 1500 mL of toluene/methanol (5:2) to give 0.5 g of the title compound; DCI NH₃ MS M/Z: 698 (M+H)⁺; IR (0.15% in CCl₄) 3555 and 1725 cm⁻¹.

Step 3: [2R-(2R*,3R*,4R*,5R*,8R*,9S*,10S*,11R*, 12R*)]-9-[( 2,6-Dideoxy-3-C-methyl- 3-O-methyl-α-L-ribo-hexopyranosyl)oxy]-5-ethyl-3,4-dihydroxy-2,4,8,10, 12,14-hexamethyl-11-[[3,4,6-trideoxy-3-(dimethylamino)-β-D-xylo-hexopyranosyl]oxy]-6-aza-15-oxabicyclo[10.2.1]pentadec-14-en-7-one

[2R-[2R*,3R*(1R*,2S*), 6R*,7S*,8S*,9R*, 10R*]]-7-[(2,6-Dideoxy-3-C-methyl-3-O-methyl-α- L-ribohexopyranosyl)oxy]- 3-(1,2-epoxy-1-methylbutyl)-2,6,8,10, 12-pentamethyl- 9-[[3,4,6-trideoxy-3-(dimethylamino)-βD-xylo-hexopyranosyl]oxy]-4,13-dioxabicyclo[8.2.1 ]tridec-12-en-5-one (2.00 g, 2.87 mmol), from Step 2, was dissolved in 16 mL of methanol, in a heavy-walled glass reaction tube. To the resultant solution was added 4.0 mL of concentrated ammonium hydroxide (59.2 mmol ammonia, 20.6 equivalents). The tube was sealed with a Teflon® "O" ring-type-screw plug. The reaction mixture was then heated to 90°–92° C. in an oil bath. The progress of the reaction was followed by HPLC using a YMC reverse phase R-ODS- 7 HPLC column eluted at 1.00 mL/minute with 60% aqueous methanol containing 10 g/L of ammonium acetate trihydrate, 25 mL/L glacial acetic acid and 50 mL/L of tetrahydrofuran. After 6 days, the reaction mixture was cooled to ambient temperature and then diluted with 250 mL of 8% aqueous sodium bicarbonate solution. The pH of the solution was brought to 10 by the addition of 10 mL of concentrated ammonium hydroxide and the basic solution was extracted with 3×50 mL portions of chloroform. The combined chloroform extracts were washed with 50 mL of a 1:1 solution of 8% aqueous sodium bicarbonate and brine, dried over anhydrous sodium sulfate, filtered and concentrated in vacuo in a water bath at 45° C. The residue was dried at 25° C. under vacuum for 3 hours to give 2.277 g of crude product. A column of silica gel (100 g), which had been washed with 1 L of 40% methanol in acetonitrile containing 2% concentrated ammonium hydroxide and 1 L of 0.1% concentrated ammonium hydroxide in acetonitrile, was equilibrated with 0.5 L of the eluent, 10% acetonitrile in chloroform containing 3.0% methanol and 0.3% concentrated ammonium hydroxide. The crude product was then chromatographed, eluting at 2.5 mL/minute. The fractions containing the desired product were combined and concentrated in vacuo in a water bath at 45° C. The residue was dissolved in 50 mL of methanol and the resultant solution was filtered and concentrated in vacuo to give, after drying in vacuo at 25° C. for 3 days, 1.752 g (85.4% yield) of the title compound. A sample was crystallized from acetonitrile at −25° C. to give needle-like crystals, m.p. 152°–156° C. after drying at 1 Torr/100° C.; $[\alpha]_D^{23} = 39.2°$ (c 1.00; MeOH)

EXAMPLE 2

[2R-(2R*,3R*,4R*,5R*,8R*,9S*,10S*,11R*,12R*)]-9-(2,6-Dideoxy-3-C-methyl-3-O-methyl-α-L-ribo-hexopyranosyl)oxy]-5-ethyl-3,4-dihydroxy-2,4,8,10,12,14-hexamethyl-11-[[3,4,6-trideoxy-3-(dimethylamino)-β-D-xylo-hexopyranosyl]oxy]-6-aza-15-oxabicyclo[10.2.1]pentadec-14-en-7-one Step 1: 2'-O-Acetyl-4"-O-benzyloxycarbonylerythromycin A 2'-O-Acetylerythromycin A (30 g, 38.6 mmol), the product of Step 1 of Example 1, was dissolved in 150 mL of methylene chloride. Dimethylaminopyridine (18.3 g, 149.8 mmol) was added and the solution was cooled to −40° C. in an acetonitrile/dry ice bath. Benzyloxycarbonyl chloride (16.8 mL, 110 mmol) was added and the solution was stirred at −40° C. until a gel formed. After keeping the reaction mixture at −25° C. for 3 days, the mixture was poured into a separatory funnel and was washed with phosphate buffer (pH 5.0). The organic layer was washed with 5% aqueous sodium bicarbonate. The aqueous sodium bicarbonate layer was extracted with methylene chloride. The combined organic layers were washed with brine, dried over anhydrous sodium sulfate, filtered and concentrated to an off-white glass. The glass was recrystallized from acetonitrile to give 21.39 g (61% yield) of the title compound; DCI NH₃ MS M/Z: 910.

Step 2: 2'-O-Acetyl-4"-O-benzyloxycarbonyl-8.9-didehydro- 9-deoxo-6-deoxy-6.9epoxyerythromycin A 2'-O-Acetyl-4"-O-benzyloxycarbonylerythromycin A (21.29 g, 23.37 mmol), from Step 1, was dissolved in 115 mL of glacial acetic acid and the resultant solution was stirred at ambient temperature for 2 hours. The acetic acid was azeotropically removed in vacuo using toluene. The residue was dissolved in 500 mL of ethyl acetate and the ethyl acetate solution was washed with a mixture of 300 mL of 5% aqueous sodium bicarbonate solution and 10 mL of ammonium hydroxide. The aqueous layer was extracted with 100 mL of ethyl acetate. The combined organic layers were washed with brine, dried over anhydrous sodium sulfate, filtered and concentrated in vacuo to give 19.39 g (93% yield) of the title compound as a white glass; DCI NH₃ MS M/Z: 892.

Step 3: [2R-[2R*,3R*(1R*,2R*),6R*,7S*,8S*,9R*,10R*]]-9-[[2-O-Acetyl-3,4,6-trideoxy- 3-(dimethylamino)-β-D-xylo-hexopyranosyl]oxy]-7-[(4-O-benzyloxycarbonyl- 2,6-dideoxy-3-C-methyl-3-O-methyl-α-L-ribo-hexopyranosyl)oxy]- 3-(1,2-dihydroxy-1-methylbutyl)-2,6,8,10,12-pentamethyl-4,13dioxabicyclo[8.2.1 ]tridec-12-en-5-one Following the procedures described in Step 3 of Example 1, and purifying the product by chromatography on silica gel eluted with toluene/acetone (5:1) followed by toluene/acetone (10:3), 5.3 g (5.95 mmol) of the product of Step 2 above was treated with potassium carbonate in DMF to give 1.46 g (28% yield) of the title compound; DCI NH₃ MS M/Z: 892; IR (5% in CDCl₃) 3595, 3560 and 1740 cm⁻¹.

Step 4: [2R-[2R*,3R*(1S*),6R*,7S*,8S*,9R*,10R*]]-9-[ [2-O-Acetyl-3,4,6-trideoxy-3-dimethylamino)-β-D-xylo-hexopyranosyl]oxy]- 7-[(4-O-benzyloxycarbonyl-2.6-dideoxy- 3-C-methyl-3-O-methyl-α-L-ribo-hexopyranosyl)oxy]-3-(1-hydroxy- 1-methyl- 2-oxobutyl)-2,6,8,10,12-pentamethyl-4,13-dioxabicyclo[8.2.1]tridec-12-en-5-one N-chlorosuccinimide (0.57 g, 4.27 mmol) was dissolved in 5.05 mL of toluene and the resultant solution was cooled to −10° C. Dimethyl sulfide (0.41 mL, 5.58 mmol) was added and the solution was stirred at −10° C. for 20 minutes. A solution of [2R-[2R*,3R*(1R*,2R*), 6R*,7S*,8S*,9R*, 10R*]]-9-[[2-O-acetyl-3,4,6-trideoxy-3'- (dimethylamino)-β- D-xylo-hexopyranosyl]oxy]-7-[(4-O-benzyloxycarbonyl- 2,6-dideoxy- 3-C-methyl-3-O-methyl-α-L-ribo-hexopyranosyl)oxy]-3-(1,2-dihydroxy-1-methylbutyl)- 2,6,8, 10,12-pentamethyl-4,13-dioxabicyclo[8.2.1 ]tridec-12-en-5-one (0.5 g, 0.56 mmol), from Step 3, in 1.28 mL of toluene was added and the reaction mixture was stirred at −40° C. for 3.5 hours. The reaction was then quenched by the addition of triethylamine and the reaction mixture was transferred to a separatory funnel and a 5% aqueous sodium bicarbonate solution was added. The aqueous layer was extracted with 4×50 mL of toluene and once with 50 mL of methylene chloride. The combined organic layers were washed with brine, dried over anhydrous sodium sulfate, filtered and concentrated in vacuo to give 0.455 g (91% yield) of the title compound; DCI NH₃ MS M/Z: 890; IR (5% in CDCl₃) 3540 and 1740 cm⁻¹.

Step 5: [2R-[2R*,3R *(1S*),6R*,7S*,8S*,9R*,10R*]]-7-[( 2.6-Dideoxy-3-C-methyl-3-O-methyl-α-L-ribo-hexopyranosyl)oxy]- 3-(1-hydroxy-1-methyl-2-oxobutyl)-2,6,8,10, 12-pentamethyl-9-[[3,4,6-trideoxy-3,(dimethylamino)-β-D- xylo-hexopyranosyl]oxy]-4,13-dioxabicyclo[8.2.1]tridec-12-en-5-one

[2R-[2R*,3R*(1S*), 6R*,7S*,8S*,9R*, 10R*]]-9-[[2-O-Acetyl-3,4,6-trideoxy-3-dimethylamino)-β-D-xylo-hexopyranosyl]oxy]-7-[(4-O-benzyloxycarbonyl-2,6-dideoxy- 3-C-methyl-3-O-methyl-α-L-ribo-hexopyranosyl)oxy]-3-(1-hydroxy-1 -methyl- 2-oxobutyl)-2,6,8,10,12-pentamethyl-4, 13-dioxabicyclo[8.2.1]tridec-12-en-5-one (3.57 g, 4.02 mmol), from Step 4, was dissolved in 200 mL of methanol. To this solution was added 3.57 g of 10% palladium on carbon. The reaction mixture was shaken at ambient temperature under 4 atmospheres of hydrogen for 24 hours. The catalyst was removed by filtration and the filtrate was concentrated in vacuo. The residue (2.5 g) was dissolved in 200 mL of methylene chloride. The methylene chloride solution was washed with 100 mL of 5% aqueous sodium bicarbonate. The aqueous wash was extracted with 3×50 mL of methylene chloride. The combined organic layers were washed with brine, dried over anhydrous sodium sulfate, filtered and concentrated in vacuo to give 2.01 g (70% yield) of the title compound; FAB MS M/Z: 714 (M+H)⁺.

Step 6: [2R-[2R*,3R*(1R*),6R*,7S*,8S*,9R*,10R*]]-7-[(2,6-Dideoxy-3-C-methyl-3-O-methyl-α-L-ribo-hexopyranosyl)oxy]-3-(1-hydroxy-1-methyl-2-oximidobutyl)-2,6, 8,10,12-pentamethyl-9-[[3,4,6-trideoxy-3-(dimethylamino)-β-D-xylo-hexopyranosyl]oxy]-4,13-dioxabicyclo[8.2.1]tridec-12-en-5-one

[2R-[2R*,3R*(1S*), 6R*,7S*,8S*,9R*, 10R*]]-7-[( 2,6-Dideoxy-3-C-methyl-3-O-methyl-α-L-ribo-hexopyranosyl)oxy]- 3-(1-hydroxy-1-methyl-2-oxo-butyl)2,6,8,10,12-pentamethyl-9-[[3,4,6-trideoxy-3-(dimethylamino)-β-D-xylo-hexopyranosyl]oxy]-4,13-dioxabicyclo[8.2.1]tridec-12-en-5-one (0.5 g, 0.7 mmol), from Step 5, was dissolved in 10 mL of ethyl alcohol. To this solution was added 0.39 g (6.05 mmol) of hydroxylamine hydrochloride and 0.6 mL (4.23 mmol) of triethylamine. The reaction mixture was heated at reflux temperature for 84 hours. The reaction mixture was allowed to cool to ambient temperature and then it was poured into a separatory funnel along with 200 mL of methylene chloride and washed with 100 mL of 5% aqueous sodium bicarbonate. The aqueous layer was extracted with 2×50 mL of methylene chloride, washed with brine, dried over anhydrous sodium sulfate, filtered and concentrated in vacuo. The residue (200 mg out of total of 410 mg) was chromatographed on 50 g of silica gel eluted with chloroform/methanol/ammonia (10:1:0.015) to give 77.8 mg of the title compound; FAB MS M/Z: 729 (M+H)⁺; IR (0.15% in CCl₄)3595 and 1733 cm⁻¹.

Step 7: [2R,(2R*,3R*,4R*,5R*,8R*,9S*,10S*,11R*,12R*)]-9-[(2,6-Dideoxy-3-C-methyl- 3-O-methyl-α-L-ribo-hexopyranosyl[oxy]-5-ethyl-3,4-dihydroxy- 2,4,8,10,12,14-hexamethyl-11-[[3,4,6-trideoxy-3-(dimethylamino)-β-D-xylo-hexopyranosyl]oxy]-6-aza- 15-oxabicyclo[10.2.1]pentadec-14-en-7-one A mixture of 100 mg (0.137 mmol) of [2R-[2R*,3R*( 1 R*),6R*,7S*,8S*,9R*, 10 R*]]-7-[(2,6-dideoxy-3-C-methyl- 3-O-methyl-L-ribo-hexopyranosyl)oxy]-3-( 1-hydroxy- 1-methyl-2-oximidobutyl)-2,6,8,10,12-pentamethyl-9-[[3,4,6-trideoxy- 3-(dimethylamino)-β-D-xylo-hexopyranosyl]oxy]-4,13-dioxabicyclo [8.2.1]tridec-12-en-5-one, 0.56 g of Raney nickel and 10 mL of ammonia in 90 mL of methanol was shaken at ambient temperature under 4 atmospheres of hydrogen for 24 hours. The catalyst was removed by filtration and the filtrate was concentrated in vacuo to a foam. The foam was dissolved in 50 mL of methylene chloride and washed with 30 mL of 5% aqueous sodium bicarbonate. The aqueous layer was extracted with 3×25 mL of methylene chloride. The combined organic layers were washed with brine, dried over anhydrous sodium sulfate, filtered and concentrated in vacuo to give 99.8 mg of the title compound; LSIMS/NBA, DMF M/Z: 715 (M+H)⁺; IR (0.15% in CCl4)3560, 3440, 3355, 1703 and 1660 cm⁻¹.

EXAMPLE 3

[2R,(2R*,3S*,4S*,5R*,8R*,9S*,10S*,11R*,12R*)]-9- [( 2,6-Dideoxy-3-C-methyl-3-O-methyl-α-L-ribo-hexopyranosyl)oxy]-5-ethyl-3-hydroxy-2,4,8, 10,12,14-hexamethyl-11-[[3,4,6-trideoxy-3-(dimethylamino)-β-D-xylo-hexopyranosyl]oxy]-6-aza-15-oxabicyclo[10.2.1]pentadec-14-en-7-one Step 1: 2'-O-Acetylerythromycin B Following the procedures described in Step I of Example 1, replacing erythromycin A with erythromycin B, the title compound was prepared.

Step 2: 2'-O-Acetyl-4''-O-benzyloxycarbonylerythromycin B

A mixture of 30.60 g (40.264 mmol) of 2'-O-acetylerythromycin B and 15.00 g (122.78 mmol) of dimethylaminopyridine (DMAP) was dissolved in 75 mL of methylene chloride. The resultant solution was cooled to −25° C. in a dry ice/CCl₄ bath. Benzylchloroformate (11.5 mL, 56.41 mmol) was added and the mixture was stored at −25° C. overnight. TLC analysis indicated incomplete reaction, therefore, DMAP (7.5 g) and benzylchloroformate (6 mL) were added and the mixture stirred at −25° C. for 6 hours. The reaction mixture was then diluted with 400 mL of ethyl acetate and was washed sequentially with 2×100 mL of 4% aqueous sodium bicarbonate, 100 mL of brine, 3×100 mL of 10% aqueous potassium dihydrogen phosphate/brine (4:1), 100 mL of brine and 100 mL of 4% aqueous sodium bicarbonate solution. The ethyl acetate solution was dried over anhydrous sodium sulfate, filtered and concentrated in vacuo to a semi-solid glass. The residue (45.14 g) was triturated with 300 mL of heptane to give 33.44 g (93% yield) of the title compound.

Step 3: [2R-[2R*,3S*,(1S*,2R*),6R*,7S*,8S*,9R*, 10R*]] -7-[(4-O-Benzyloxycarbonyl- 2,6-dideoxy-3-C-methyl-3-O-methyl-α-L-ribo-hexopyranosyl)oxy]-3-(2-hydroxy-1-methylbutyl)- 2,6,8,10,12-pentamethyl-9-[[3,4,6-trideoxy-3-(dimethylamino)-β-D-xylo-hexopyranosyl]oxy]-4,13-dioxabicyclo[8.2.1]tridec-12-en-5-one 2'-O-Acetyl-4''-O-benzyloxycarbonylerythromycin B (10.11 g, 11.307 mmol) was dissolved in 250 mL of methanol and the solution was allowed to stand at 25° C. for 3 days. Glacial acetic acid (5.43 mL (94.92 mmol) was added and the resultant mixture was heated at reflux temperature for 48 hours. The reaction was then cooled to ambient temperature and 6.41 mL (94.92 mmol) of concentrated ammonium hydroxide was added. The reaction mixture was heated at reflux temperature for 9 days. The reaction mixture was concentrated to 25 mL and then diluted with 300 mL of 4% aqueous sodium bicarbonate. The aqueous mixture was extracted with 1×100 mL of chloroform followed by 2×50 mL of chloroform. The combined organic extracts were washed with 100 mL of 4% aqueous sodium bicarbonate, dried over anhydrous sodium sulfate, filtered and concentrated in vacuo. Acetonitrile was added to the residue to azeotropically remove residual chloroform and water and evaporated under reduced pressure to give 8.91 g of the title compound which was taken on to the next step without purification.

Step 4: [2R-[2R*,3S*(1S*,2R*),6R*,7S*,8S*,9R*,10R*]]-9-[[2-O-Acetyl-3,4,6-trideoxy- 3-(dimethylamino)-β-D-xylo-hexopyranosyl]oxy]-7-[( 4-O-benzyloxycarbonyl- 2.6-dideoxy-3-C-methyl-3-O-methyl-α-L-ribo-hexopyranosyl)oxy]- 3-(2-hydroxy-1-methylbutyl)-2,6,8, 10,12-pentamethyl-4,13dioxabicyclo[8.2.1 ]tridec-12-en-5-one

[2R-[2R*,3S*(1S*,2R*), 6R*,7S*,8S*,9R*, 10R*]]-7-[(4-O-Benzyloxycarbonyl- 2,6-dideoxy-3-C-methyl-3-O-methyl-α-L-ribo-hexopyranosyl)oxy]-3-(2-hydroxy-1-methylbutyl)- 2,6,8,10,12-pentamethyl-9-[[3,4,6-trideoxy-3-(dimethylamino)-β-D-xylo-hexopyranosyl]oxy]-4,13-dioxabicyclo[8.2.1 ]tridec-12-en-5-one (8.84 g, 10.599 mmol), from Step 3, was dissolved in 175 mL of methylene chloride. Acetic anhydride (3.5 mL) and triethylamine (9 mL) were added and the reaction mixture was allowed to stand at ambient temperature for 2.5 days. The reaction mixture was concentrated in vacuo and the residue was dissolved in 200 mL of ethyl acetate. The ethyl acetate solution was washed with 4×50 mL of 4% aqueous sodium bicarbonate solution. Solid sodium chloride (20 mL) was added to each of the second, third and fourth washes to improve the phase separation. The ethyl acetate solution was dried over sodium sulfate, filtered and concentrated in vacuo to give 9.12 g of the title compound as a white glass; IR (0.15% in $CCl_4$): 3530, 1748 and 1718 $cm^{-1}$.

Step 5: [2R-[2R*,3R*(1R),6R*,7S*,8S*,9R*,10R*]]-9-[ [(dimethylamino)-β-D-xylo-hexopyranosyl]oxy]-7-[4-O-benzyloxycarbonyl- 2.6-dideoxy- 3-C-methyl-3-O-methyl-α-L-ribo-hexopyranosyl)oxy]-2,6,8,10,12-pentamethyl-3-(1-methyl-2-oxobutyl)-4,13-dioxabicyclo[8.2.1]tridec-12-en-5-one A mixture of 5.197 g (5.932 mmol) of [2R-[2R*, 3S*(1S*,2R*),6R*,7S*, 8S*,9R*, 10R*]]-9-[[2-O-acetyl-3,4,6-trideoxy- 3-(dimethylamino)-β-D-xylo-hexopyranosyl]oxy]-7-[(4-O-benzyloxycarbonyl-2, 6-dideoxy-3-C-methyl- 3-O-methyl-α-L-ribo-hexopyranosyl)oxy]- 3-(2-hydroxy-1 -methylbutyl)-2,6,8,10,12-pentamethyl- 4,13-dioxabicyclo[8.2.1 ]tridec-12-en-5-one from Step 4, 4.20 g (35.85 mmol) of N-methylmorpholine N-oxide and 2.5 g of 4 A molecular sieves in 26 mL of methylene chloride was stirred at 20° C. for 1 hour. The reaction mixture was then cooled to −15° C. in an ice/acetone bath and after 15 minutes, 30.9 mg (0.879 mmol) of tetrapropyl-ammonium perruthenate was added. After stirring for several minutes at −15° C. the reaction was allowed to stand at −15° C. for 20 hours. The reaction mixture was then filtered into a stirred mixture of 11 g of sodium bisulfite in 100 mL of water, using 200 mL of ethyl acetate to wash the filter cake. The filtrate was diluted with 100 mL of water and after vigorously stirring for 1 hour was filtered. The aqueous layer was separated and discarded. The organic layer was washed with 2×100 mL of a 50/50 mixture of brine and 4% aqueous sodium bicarbonate. The ethyl acetate solution was dried over anhydrous sodium sulfate, filtered and concentrated in vacuo to give 4.65 g (90% yield) of the title compound as a white glass.

Step 6: [2R-[2R*,3R*(1R*)6R*,7S*,8S*,9R*, 10R*]]-7-[(4-O-Benzyloxycarbonyl-2,6-dideoxy- 3-C-methyl-3-O-methyl-α-L-ribo-hexopyranosyl)oxy]-2,6,8,10,12-pentamethyl- 3-(1-methyl-2-oxobutyl)-9-[[3,4,6-trideoxy-3-(dimethylamino)-β-D-xylo-hexopranosyl]oxy]-4,13-dioxabicyclo[8.2.1 ]tridec-12-en-5-one

[2R-[2R*,3R*(1R*), 6R*,7S*,8S*,9R*,10R*]]-9-[[2-O-Acetyl-3,4,6-trideoxy- 3-(dimethylamino)-β-D-xylo-hexopyranosyl]oxy]-7-[(4-O-benzyloxycarbonyl- 2,6-dideoxy-3-C-methyl-3-O-methyl-α-L-ribo-hexopyranosyl[oxy]-2,6, 8,10,12-pentamethyl- 3-(1 -methyl-2-oxobutyl)-4,13-dioxabicyclo[8.2.1 ]tridec-12-en-5-one (4.65 g, 5.3 mmol), from Step 5, was dissolved in 100 mL of methanol and kept at 25° C. for 4 days. A small amount of precipitate was removed by filtration and the solvent was removed in vacuo. The dried residue (4.39 g) was chromatographed on 200 g of silica gel which had been preconditioned and was eluted with ethyl acetate/heptane/ammonium hydroxide (69.8:30:0.2) to give 1.57 g (35% yield) of the title compound as a white foam.

Step 7: [2R-[2R*,3R*(1R*),6R*,7S*,8S *,9R*,10R*]]-7-[(2,6-Dideoxy-3-C-methyl- 3-O-methyl-α-L-ribo-hexopyranosyl)oxy]-2,6,8,10,12-pentamethyl-3-(1 -methyl- 2-oxobutyl)-9-[[3,4,6-trideoxy-3-(dimethylamino)-βD-xylo-hexopyranoyl]oxy]-4,13dioxabicyclo[8.2.1 ]tridec-12-en-5-one

[2R-[2R*,3R*(1R*), 6R*,7S*,8S*,9R*, 10R*]]-7-[(4-O-Benzyloxycarbonyl- 2,6-dideoxy-3-C-methyl-3-O-methyl-α-L-ribo-hexopyranosyl)oxy]-2,6,8,10,12-pentamethyl- 3-(1-methyl-2-oxobutyl)-9-[[3,4,6-trideoxy-3-(dimethylamino)-β-D-xylo-hexopyranosyl]oxy]- 4,13-dioxabicyclo[8.2.1 ]tridec-12-en-5-one [8.2.1 ]tridec-12-en-5-one (1.52 g, 1.83 mmol) was dissolved in 100 mL of methanol. To the resultant solution was added 75 mg of 10% palladium on carbon. The reaction mixture was shaken at ambient temperature under 4 atmospheres of hydrogen for 1 hour. TLC analysis on silica gel plates eluted with chloroform/methanol/concentrated ammonium hydroxide (9.5:0.5:0.2) indicated that the reaction was complete. The catalyst was removed by filtration and the filter cake was washed with 100 mL of methanol. The filtrate was concentrated under reduced pressure to give 1.267 g (99% yield) of the title compound.

Step 8: [2R-[2R*,3S*(1S*),6R*,7S*,8S*,9R*,10R*]]-7-[(2,6-Dideoxy-3-C-methyl- 3-O-methyl-α-L-ribo-hexopyranosyl)oxy]-2,6,8,10,12-pentamethyl-3-(1-methyl-2-oximidobutyl)-9-[[3,4,6-trideoxy-3-(dimethylamino)-β-D-xylo-hexopyranosyl]oxy]- 4,13-dioxabicyclo[8.2.1] tridec-12-en-5-one

[2R-[2R*,3R*(1R*), 6R*,7S*,8S*,9R*, 10R*]]-7-[(2,6-Dideoxy-3-C-methyl- 3-O-methyl-α-L-ribo-hexopyranosyl)oxy]-2,6,8,10,12-pentamethyl-3-(1-methyl-2-oxobutyl)-9-[[3,4,6-trideoxy-3-(dimethylamino))-β-D-xylo-hexopyranosyl]oxy]-4,13dioxabicyclo[8.2.1]tridec-12-en-5-one (1.211 g, 1.735 mmol), from Step 7, was dissolved in 82 mL of absolute ethyl alcohol. To this solution was added 601 mg (8.65 mmol) of hydroxylamine hydrochloride, followed by 725 μL (5.18 mmol) of triethylamine. The reaction mixture was heated at reflux temperature and monitored by analytical HPLC on a YMC reverse phase AQ-303 column eluted at 1 mL/min with water/acetonitrile/methanol (5:4.5:0.5) containing 6.5 g/L of ammonium acetate. After 18 hours, the reaction mixture was concentrated to a few mLs. Ethyl acetate (150 mL) and 33 mL of 8% aqueous sodium bicarbonate solution were added. The organic layer was washed with 2×33 mL of 8% aqueous sodium bicarbonate, dried over anhydrous sodium sulfate, filtered and concentrated in vacuo. The residue was carried on to the next step without purification.

Step 9: Diastereomeric mixture of [2R-[2R*,3S*(1S*,2R*), 6R*,7S*,8S*, 9R*,10R*]]-3-(2-amino-1-methylbutyl)-7-[(2.6-dideoxy-3-C-methyl- 3-O-ribo-hexopyranosyl)oxy]-2,6,8,10,12-pentamethyl-9-]]3,4,6-trideoxy, 3-(dimethylamino)-β-D-xylo-hexopyranosyl]oxy]-4,13,dioxabicyclo [8.2.1]tridec-12-en-5-one and

[2R,[2R*,3S*(1S*,2S *),6R*,7S*,8S*,8S*,9R*,10R*]]-3-(2-amino-1-methylbutyl)-7-[( 2,6-deoxy-3-C-methyl-3-

O-methyl-α-L-ribo-hexopyranosyl)oxy]-2,6,8,10,12,pentamethyl- 9-[[3,4,6-trideoxy,3-(dimethylamino)-β-D-xylo-hexopyranosyl]oxy]- 4,13-dioxabicyclo[8.2.1]tridec-12-en-5-one

[2R-[2R*,3S*(1S*), 6R*,7S*,8S*,9R*, 10R*]]-7-[(2,6-Dideoxy-3-C-methyl- 3-O-methyl-α-L-ribo-hexopyranosyl)oxy]-2,6,8,10,12-pentamethyl-3-(1-methyl-2-oximidobutyl)-9-[[3,4,6-trideoxy-3-(dimethylamino)-β-D-xylo-hexopyranosyl]oxy]4,13-dioxabicyclo[8.2.1]tridec-12-en-5-one (997 mg), from Step 8, was dissolved in 10% ammonium hydroxide in 100 mL of methanol. To this solution was added 2.5 g of Raney nickel and the reaction mixture was shaken at ambient temperature under 4 atmospheres of hydrogen for 18 hours. The catalyst was removed by filtration and the filtrate was concentrated under reduced pressure. The dry residue (895 mg) was dissolved in 120 mL of ethyl acetate and the ethyl acetate solution was washed with 3×33 mL of 8% aqueous sodium bicarbonate solution and 30 mL of brine, dried over anhydrous sodium sulfate, filtered and concentrated in vacuo to give 799 mg of the title mixture as a white glass. The product was carried on to the next step without purification.

Step 10: [2R-(2R*,3S*,4S*,5R*,8R*,9S*,10S*,11R*,12R*)]- 9-[(2,6-Dideoxy- 3-C-methyl-3-O-methyl-α-L-ribo-hexopyranosyl)oxy]-5-ethyl-3-hydroxy-2,4,8,10,12,14-hexamethyl- 11-[[3,4,6-trideoxy-3-(dimethylamino)-β-D-xylo-hexopyranosyl]oxy]- 6-aza-15-oxabicyclo[10.2.1]pentadec-14-en-7-one The diastereomeric mixture of [2R-[2R*,3S*(1S*, 2R*),6R*,7S*,8S*,9R*,10R*]]-3-(2-amino-1-methylbutyl)-7-[(2,6-dideoxy-3-C-methyl-3-O-methyl-α-L-ribo-hexopyranosyl)oxy]- 2,6,8,10,12-pentamethyl-9-[[3,4,6-trideoxy- 3-(dimethylamino)-β-D-xylo-hexopyranosyl]oxy]- 4,13-dioxabicyclo[8.2.1 ]tridec-12-en-5-one and [2R*-[2R*,3S*(1S*,2S*), 6R*,7S*,8S*,9R*, 10R*]]-3-(2-amino-1-methylbutyl)-7-[( 2,6-dideoxy-3-C-methyl-3-O-methyl-α-L-ribo-hexopyranosyl)oxy]-2,6,8,10,12-pentamethyl- 9-[[3,4,6-trideoxy-3-(dimethylamino)-β-D-xylo-hexopyranosyl]oxy]4,13-dioxabicyclo[8.2.1 ]tridec-12-en-5-one (345.1 mg) was dissolved in 9.0 mL of methanol. To this solution was added 1.0 mL of concentrated ammonium hydroxide and the resultant solution was heated at 45° C. in a screw capped vial for 9 days. The solution was concentrated in vacuo to give 338.6 of a glass. The glass (300 mg) was dissolved in 2.0 mL of methanol and purified by preparative HPLC chromatography. The HPLC column, a D-ODS-7 (20×250 cm) C8 reverse phase column was eluted at 14 mL/min. The eluent was prepared by dilution of 36 g of ammonium acetate with 2.1 L of water and 1 L of acetonitrile. The methanol solution was filtered through a 45 μ nylon filter and injected onto the column in 5 batches (4×400 μL and 1×200 μL). The first peak to elute from the column (fraction A; RT=18.6 min) was collected in a flask containing 150 mL of 1N aqueous ammonium hydroxide. The second peak to elute from the column (fraction B) was collected at 22.8 min. Each fraction was separately concentrated in vacuo at 45° C. to remove acetonitrile. 10% Aqueous sodium carbonate solution (25 mL) was added to the resulting aqueous mixture which was extracted with 5×20 mL of chloroform. The combined chloroform extracts were washed with a mixture of 15 mL of brine and 2 mL of concentrated ammonium hydroxide, dried over anhydrous sodium sulfate, filtered and concentrated in vacuo. Acetonitrile was added to the residue to azeotropically remove residual chloroform and water and evaporated under reduced pressure to give 65.4 mg (19% yield) of Fraction A (the title compound) and 105 mg (31% yield) of Fraction B (the 2S*-2-amino diastereomer). Fraction A: FAB MS M/Z: 699 (M+H)$^+$; IR (0.15% in CCl$_4$) 3565, 3480, 1650 cm$^{-1}$. Fraction B: FAB MS M/Z: 699 (M+H)$^+$; IR (0.15% in CCl$_4$) 3558, 3470, 1720 cm$^{-1}$.

EXAMPLE 4

[2R-(2R*,3R*,4R*,5R*,8R*,9S*, 10S*,11R*,12R*)]-9-[(2,6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(methylamino)-β-D-xylo-hexopyranosyl]oxy]aza-15-oxabicyclo[10.2.1]pentadec-14-en-7-one

[2R-(2R*,3R*,4R*,5R*, 8R*,9S*,10S*,11R*,12R*)]-9-[( 2,6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(dimethylamino)-β-D-xylo-hexopyranosyl]oxy]- 6-aza-15-oxabicyclo[10.2.1]pentadec-14-en-7-one (2 g, 2.8 mmol), the product of Example 1, was dissolved in 40 mL of methanol. To this solution at ambient temperature was added 1.9 g (14 mmol) of sodium acetate, followed by 390 mg (1.54 mmol) of iodine, and the resultant solution was exposed to light for 45 minutes. The iodine color was no longer visible. A second portion of iodine (390 mg, 1.54 mmol) was added and the solution again exposed to light for 1.5 hours. The reaction mixture was then poured into a separatory funnel containing 50 ml of methylene chloride and washed with a mixture of approximately 21 mL of brine and 50 mL of 5% aqueous sodium bicarbonate solution containing 100 mg of sodium thiosulfate. The aqueous layers were extracted with 5×25 mL of methylene chloride. The combined organic layers were washed with brine, dried over anhydrous sodium sulfate, filtered and concentrated in vacuo. The residue (1.82 g) was chromatographed on 150 g of silica gel eluted with chloroform/methanol/ammonia (100:3:0.3) to give 865 mg (44% yield) of the title compound; FAB MS M/Z: 701 (M+H)$^+$; IR (0.15% in CCl$_4$) 3560, 3438, 3353 and 1660 cm$^{-1}$.

In another run, the solvent used for workup was ethyl acetate instead of methylene chloride, and the product was crystallized from acetonitrile, instead of being purified by chromatography. mp 170°–175° C. [α]$_D$=29.0° (c=1.00, MeOH, 28° C.). IR (CCl$_4$) 963, 1665, 1700 cm$^{-1}$. Anal Calc. for C$_{36}$H$_{64}$N$_2$O$_{11}$C, 61.69H, 9.20; N, 4.00; Found: C, 61.39; H, 9.02; N, 3.95.

EXAMPLE 5

[2R-(2R*,3R*,4R*,5R*,8R*,9S*, 10S*,11R*,12R*)]-9-[(2.6-Dideoxy-3-C-methyl 3-O-methyl-α-L-ribo-hexopyranosyl)oxy]-5-ethyl-3, 4-dihydroxy-2,4,8,10,12,14-hexamethyl- 11-[[3,4,6-trideoxy-3-(ethylmethylamino)-β-D-xylo-hexopyranosyl]oxy]6-aza-15-oxabicyclo[10.2.1]pentadec-14-en-7-one

[2R-(2R*,3R*,4R*,5R*, 8R*,9S*,10S*,11R*,12R*)]-9-[(2,6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(methylamino)-β-D-xylo-hexopyranosyl]oxy]- 6-aza-15-oxabicyclo[10.2.1]pentadec-14-en-7-one (53 mg, 0.076 mmol), the product of Example 4, was dissolved in 3 mL of methanol. To this solution was added 25 mg of 10% palladium on carbon and 50 μL (0.82 mmol) of acetaldehyde. The reaction mixture was shaken at ambient temperature under 4 atmospheres of hydrogen for 18 hours. The catalyst was removed by filtration and the filtrate was concentrated in vacuo. The residue was washed with 50 mL of 5% aqueous sodium bicarbonate and the aqueous mixture was extracted with 3×7 mL of methylene chloride. The combined organic extracts were washed with brine and concentrated in vacuo. The residue (43.3 mg) was combined with additional material from an identical reaction (total=200 mg) and chromatographed on a 1×40 cm silica gel column eluted with toluene/methanol (20:1) to give 98.6 mg of solid. The solid was dissolved in 4 mL of acetonitrile and filtered. The filtrate was concentrated in vacuo to give 62.8 mg of the title compound; FAB MS M/Z: 729 (M+H)$^+$; IR (0.15% in CCl$_4$)3560, 3440, 3355 and 1660 cm$^{-1}$.

EXAMPLE 6

[2R-(2R*,3R*,4R*,5R*,8R*,9S*, 10S*,11R*,12R*)]-9-[(2.6-Dideoxy-3-C-methyl- 3-O-methyl-α-L-ribo-hexopyranosyl)oxy]-5- ethyl-3,4-dihydroxy-2,4,8,10,12,14-hexamethyl- 11-[ [3,4,6-trideoxy-3,(methyl(2-propenyl)amino)-β-D-xylo- hexopyranosyl]oxy]-6-aza, 15-oxabicyclo[10.2.1]pentadec-14-en-7-one

[2R-(2R*,3R*,4R*,5R*, 8R*,9S*,10S*,11R*,12R*)]- 9-[(2,6-Dideoxy-3-C-methyl- 3-O-methyl-α-L-ribo-hexopyranosyl)oxy]-5-ethyl-3,4-dihydroxy-2,4,8, 10,12,14- hexamethyl- 11-[[3,4,6-trideoxy-3-(methylamino)-β-D-xylo-hexopyranosyl]oxy]- 6-aza-15-oxabicyclo[10.2.1] pentadec-14-en-7-one (60.9 mg, 0.087 mmol), the product of Example 4, was dissolved in 1.5 mL of acetonitrile. To this solution was added 25 μL (0.289 mmol) of cold allyl bromide and the reaction mixture was stirred at ambient temperature for approximately 8 hours. The reaction mixture was diluted with 50 mL of 5% aqueous sodium bicarbonate solution and was extracted with 3×15 mL of methylene chloride. The combined organic layers were washed with brine, dried over anhydrous sodium sulfate, filtered and concentrated in vacuo to a glassy solid. The glass (54.8 mg) was purified by chromatography on silica gel eluted with toluene/methanol (20:1) to give 19.6 mg (31% yield) of the title compound; FAB MS M/Z: 741 (M+H)$^+$.

EXAMPLE 7

[2R-(2R*,3R*,4R*,5R*,8R*,9S*, 10S*,11R*,12R*)]-9-[( 2.6-Dideoxy-3-C-methyl- 3-O-methyl-α-L-ribo-hexopyranosyl)oxy]- 5-ethyl-3,4-dihydroxy-2,4,8,10,12,14-hexamethyl- 11-[[3,4,6-trideoxy-3-(dimethyl(2-propenyl) ammonium)-β-D-xylo-hexopyranosyl]oxy]- 6-aza-15-oxabi-cyclo[10.2.1]pentadec-14-en-7-one bromide

[2R-(2R*,3R*,4R*,5R*, 8R*,9S*,10S*,11R*,12R*)]- 9-[(2,6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(dimethylamino)-β-D-xylo-hexopyranosyl]oxy]- 6-aza-15-oxabicyclo[10.2.1]pentadec-14-en-7-one (200 mg, 0.28 mmol), the product of Example 1, was dissolved in 3 mL of acetonitrile. To this solution was added 80 μL (0.924 mmol) of allyl bromide and the reaction mixture was stirred at ambient temperature for 2 hours. The reaction mixture was concentrated in vacuo. The residue was triturated with ethyl acetate. The solid phase was dried in vacuo to give 160 mg (68% yield) of the title compound; FAB MS M/Z: 755 (M$^+$-Br); IR (KBr) 1703, 1650 cm$^{-1}$.

EXAMPLE 8

[2R-(2R*,3R*,4R*,5R*,8R*,9S*, 10S*,11R*.12R*)]-9-[(2,6-Dideoxy-3-C-methyl- 3-O-methyl-αL-ribo-hexopyranosyl)oxy]- 5-ethyl-3,4-dihydroxy-2,4,8,10,12,14-hexamethyl- 11-3,4,6,trideoxy-3-(dimethylamino)-β- D-xylo-hexopyranosyl]oxy]- 6-aza-15-oxabicyclo[10.2.1]pentadec-14-en-7-one 13-O,14-O-carbonate

[2R-(2R*,3R*,4R*,5R*, 8R*,9S*,10S*,11R*,12R*)]- 9-[(2,6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(dimethylamino)-β-D-xylo-hexopyranosyl]oxy]- 6-aza-15-oxabicyclo[10.2.1]pentadec-14-en-7-one (177 mg, 0.248 mmol), the product of Example 1, was dissolved in 2 mL of toluene/THF (1:1 ). To this solution was added 0.37 g (2.68 mmol) of potassium carbonate, followed by 0.78 g (8.86 mmol) of ethylene carbonate (commercially available from Aldrich Chemical Company). The reaction mixture was heated at reflux temperature for 3 hours, cooled to ambient temperature, diluted with 50 mL of 5% aqueous sodium bicarbonate and extracted with 3×25 mL of toluene. The organic phase was washed with 50 mL of brine and concentrated in vacuo to an oil which solidified upon standing at ambient temperature. The residue was chromatographed on silica gel eluted with chloroform/acetonitrile/methanol/ammonia (10:2.5:0.25:0.03) to give 66.7 mg (19% yield) of the title compound; DCI NH$_3$ MS M/Z: 741 (M+H)$^+$; IR (0.15% in CCl$_4$) 3560, 3440, 3358, 1805 and 1678 cm$^{-1}$.

EXAMPLE 9

[1R,(1R*2R*,3R*,4R*,5R*,8R*, 9S*,10S*,11R*,12R*,14S*)]- 9-[(2,6-Dideoxy-3-C-methyl- 3-O-methyl-α-ribo-hexopyranosyl)oxy]- 5-ethyl-3,4-dihydroxy-2,4,8,10,12,14- hexamethyl-11-[[3,4,6-trideoxy-3- (dimethylamino)-β-D-xylo-hexopyranosyl] oxy]-6-aza-15-oxabicyclo[10.2.1]pentadecan-7-one

[2R-(2R*,3R*,4R*,5R*, 8R*,9S*,10S*,11R*,12R*)]- 9-[(2,6-Dideoxy-3C-methyl- 3-O-methyl-α-L-ribo-hexopyranosyl)oxy]-5-ethyl-3,4-dihydroxy-2,4,8, 10,12,14-hexamethyl- 11-[[3,4,6-trideoxy-3-(dimethylamino)-β-D-xylo-hexopyranosyl]oxy]- 6-aza-15-oxabicyclo[10.2.1]pentadec-14-en-7-one (21 0.7 mg, 0.295 mmol), the product of example 1, was dissolved in 20 mL of glacial acetic acid. To the resultant solution was added 40 μL (2.157 equivalents) of difluoroacetic acid (DFA) and 210 mg of platinum oxide. The reaction mixture was shaken at ambient temperature under 4 atmospheres of hydrogen for 4 hours. Ammonium acetate (160 mg) was added and the resultant mixture was shaken for 10 minutes. The catalyst was removed by filtration and the filtrate was concentrated under reduced pressure. The residue was diluted with 50 mL of chloroform. A mixture of 50 mL of brine and 10 mL of concentrated ammonium hydroxide was added. The chloroform layer was separated and the aqueous layer was extracted with 30 mL of chloroform. The combined chloroform layers were washed with a mixture 40 mL of brine and 5 mL of concentrated ammonium hydroxide. The chloroform solution was dried over anhydrous sodium sulfate, filtered and concentrated. The residue was evaporated from acetonitrile to remove all of the chloroform and dried under vacuum to give 230.4 mg of a white glass. The title compound was separated from the other components of the crude product by preparative HPLC on a reverse phase YMC D-ODS-7 column (20×250 mm) eluted at 10 mL/min with 40% methanol in water containing 10 g/L of triethylamine hydrochloride, 0.1 mL/L of glacial acetic acid and 30 mL/L of ethylene glycol. The crude product (the white glass) was dissolved in 2.0 mL of methanol and the solution was filtered through a 0.4 µL nylon filter. The methanol solution was injected onto the HPLC column in 6 portions totalling 1.755 mL. The peak collected at 14.7 min was combined from each run and concentrated to less than one half of the collected volume using a rotary evaporator and water bath heated to 45° C. The concentrate was diluted with an equal volume of brine and then made basic (pH 10) with 20 mL of 10% aqueous sodium carbonate solution. The product was extracted with 4×25 mL of chloroform. The combined extracts were washed with 30 mL of water, dried over anhydrous sodium sulfate, filtered and concentrated to dryness under reduced pressure. After vacuum drying, the residue was dissolved in 2 mL of acetonitrile and treated with 50 mg of sodium bicarbonate. After the mixture was stirred for 15 min, it was filtered and the filtrate was concentrated to dryness under a stream of nitrogen. The title compound (30.3 mg) was obtained after vacuum drying; FAB MS M/Z: 717 (M+H)$^+$; IR (0.15% in CCl$_4$) 3560, 3470, 3440, 3345 and 1660 cm$^{-1}$.

EXAMPLE 10

Reaction of
[2R-(2R*,3R*,4R*,5R*,8R*,9S*,10S*,11R*,12R*)]-
9-Dideoxy-3-C-methyl-
3-O-methyl-α-L-ribo-hexopyranosyl
[oxy]-5-ethyl-3,4-dihydroxy-
2,4,8,10,12,14-hexamethyl-11-[[3,4,6-trideoxy-
3-(dimethylamino)-β-D-xylo-hexopyranosyl]oxy]-
6-aza-15-oxabicyclo[10.2.1]pentadec-14-en-7-one
with Aqueous Acetic Acid To [2R-(2R*,3R*,4R*,5R*, 8R*,9S*,10S*,11R*,12 R*)]-9-[( 2,6S-dideoxy-3-C-methyl- 3-O-methyl-α-L-ribo-hexopyranosyl)oxy]-5-ethyl-3,4-dihydroxy-2,4,8,10,12,14-hexamethyl-11-[[3,4,6-trideoxy-3-(di-methylamino)-β-D-xylohexopyranosyl]oxy]-6-aza-15-oxabicyclo[10.2.1]pentadec-14-en-7-one (515 mg, 0.72 mmol), the product of example 1, suspended in 20 mL of water, was added 20 mL of glacial acetic acid. The reaction mixture was stirred at ambient temperature for approximately 4 hours and then poured into 300 mL of water. The solution was made basic (pH 8-9) by adding 5% sodium bicarbonate solution and ammonium hydroxide and gently swirling. The aqueous solution was poured into a separatory funnel containing methylene chloride and the methylene chloride layer was separated. The aqueous layer was extracted with 3×100 mL of methylene chloride. The combined methylene chloride extracts were concentrated under reduced pressure to give 300 mg of the acid degradation products. One of those products was identified as the corresponding anhydrous compound, [1R-(1R*,2R*, 3R*,4R*,5R*,8R*,9S*, 10 S*,11R*,12R*,14R*)]-9-[(2,6-dideoxy-3-C-methyl-3-O-methyl-α-L-ribo-hexopyranosyl)oxy]- 5-ethyl-3-hydroxy-2,4,8,10,12,14-hexamethyl-11-[[3,4,6-trideoxy-3-(dimethyl-amino)-β-D-xylo-hexopyranosyl]oxy]-6-aza-15, 16dioxatricyclo[10.2.1.1$^{1,4}$] pentadecan-7-one. A crude sample of the anhydrous compound (540 mg) was chromatographed on silica gel (approximately 100 g) equilibrated with chloroform/acetonitrile/methanol/ammonia (10:3:0.4:0.03) and eluted with chloroform/acetonitrile/methanol/ammonia (10:3:0.6:0.006) to give 100 mg of the anhydrous compound. FAB MS M/Z: 715 (M+H)$^+$; IR (0.15% in CCl$_4$) 3460, 3435, 3330 and 1645 cm$^{-1}$; $^{13}$C NMR (DMSO-d6) C9 at 114.3 ppm. [α]$_D^{23}$=−11.8° (c 1.00; MeOH). A sample was crystallized from acetonitrile, m.p. 178°–182° C.

EXAMPLE 11

Reaction of
[2R-(2R*,3R*,4R*,5R*,8R*,9S*,10S*,11R*,12R*)]-
9-[(2,6-Dideoxy-3-C-methyl-
3-O-methyl-α-L-ribo-hexopyranosyl)oxy]-5-ethyl-
3,4-dihydroxy-2,4,8,10,12,14-hexamethyl-11-[[3,4,6-
trideoxy-3-(dimethylamino)-β-D-xylo-hexopyranosyl]
oxy]-6-aza-15oxabicyclo[10.2.1]pentadec-14-en-7-one
with Aqueous Hydrochloric Acid

[2R-(2R*,3R*,4R*,5R*, 8R*,9S*,10S*,11R*,12R*)]-9-[(2,6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(dimethylamino)-β-D-xylo-hexopyranosyl]oxy]- 6-aza-15-oxabicyclo[10.2.1]pentadec-14-en-7-one (874 mg, 1.22 mmol), the product of example 1, was dissolved in acetonitrile and the solution was concentrated down to a foam under reduced pressure. Water (50 mL) was added to the foam while the sides of the flask were scraped. A solution of 2 mL of 1N aqueous hydrochloric acid in 100 mL of water was prepared and 39.33 mL of this solution was added portionwise to the aqueous erythromycin A lactam enol ether. After the addition was complete the pH of the resultant solution was 3. As sample dissolved it was necessary to adjust the pH by the addition of 1N aqueous hydrochloric acid in order to maintain the pH at approximately 2.5. After stirring for 90 minutes the reaction mixture was quenched by pouring the acidic solution into a separatory funnel with 100 mL of 5% aqueous sodium bicarbonate solution and 3 mL of concentrated ammonium hydroxide. The aqueous layer was extracted with 3×50 mL of methylene chloride. The organic layer was washed with brine, dried over anhydrous sodium sulfate, filtered and concentrated under reduced pressure. Silica gel (approximately 100 g) was slurried with acetonitrile/ammonia (10:0.5) and poured into a column. The column was equilibrated with 2 L of chloroform/acetonitrile/methanol/ammonia (10:3:0.5:0.05). The residue was loaded on the column and the column was eluted with chloroform/acetonitrile/methanol/ammonia (10:0.3:0.5:0.05) to give 160 mg of [3R-(3R*,4S*,5S*,6 R*,7R*,9S*, 11R*,12R*,13R*,14R*)]-4-[( 2,6-dideoxy-3-C-methyl-3-O-methyl-α-L-ribo-hexopyranosyl)oxy]14-ethyl-7,12,13-trihydroxy-3,5,7,9,11,13-hexamethyl- 6-[[3,4,6-trideoxy-3-(dimethylamino)-β-D-xylo-hexopyranosyl]oxy]aza-cyclotetradecane-2,10-dione (erythromycin A lactam"). FAB MS M/Z: 733 (M+H)$^+$; IR (0.15% in CCl$_4$) 3560, 3430, 1675 and 1655 cm$^{-1}$;$^{13}$C NMR (DMSO-d6) C9 at 217.2 and 107.6 (mixture of ketone and 9, 12-hemiacetal). [α]$_D^{23}$=52.9° (c1.00; MeOH).

EXAMPLE 12

[2R-(2R*,3R*,4R*,5R*,8R*,9S*,10S*,11R*,12R*)]-
9-[(2,6-Dideoxy-3-C-methyl-3-O-
methyl-α-L-ribo-hexopyranosyl)oxy]-5-
ethyl-3.4-dihydroxy-2.4.6.8.1.0,12,14-
heptamethyl-
11-[[3,4,6-trideoxy-3-(dimethylamino)-β-
D-xylo-hexopyranosyl]oxy],
6-aza-15-oxabicyclo[10.2.1]pentadec-14-en-7-one A solution of 15% methylamine in methanol was prepared by adding 15 mL of liquid methylamine in 85 mL of methanol cooled to 0° C. in an ice bath. [2R-[2R*,3R* (1 R*,2S*),6R*,7S*, 8S*,9R*,10R*]]-7-[( 2,6-Dideoxy-3-C-methyl-3-O-methyl-α-L-ribo-hexopyranosyl)oxy]- 3-(1,2-epoxy-1-methylbutyl)-2,6,8,10,12-pentamethyl- 9-[[3,4,6-trideoxy-3-(dimethylamino)-β-D-xylo-hexo-pyranosyl]oxy] -4,13-dioxabicyclo[8.2.1 ]tridec- 12-en-5-one (441.6 mg, 0.6327 mmol), from Step 4 of Example 1, was dissolved in 10 mL of the methylamine solution in a 20 mL heavy-walled reaction tube. The reaction tube was sealed with a teflon screw cap and "O" ring and then the tube was heated at 100° C. in an oil bath for 5 days. The reaction mixture was sampled and analyzed using the HPLC system described in Step 3 of Example 1 A. According to HPLC analysis, the epoxide starting material was consumed. The crude reaction material was diluted with 100 mL of 8% aqueous sodium bicarbonate solution and extracted with 3×25 mL of chloroform. The chloroform extract was washed with 50 mL of a 1:1 solution of 8% aqueous sodium bicarbonate and brine. The chloroform solution was dried over anhydrous sodium sulfate, filtered and concentrated in vacuo. The residue was dissolved in 30 mL of acetonitrile and the solvent removed in vacuo to give a dark yellow residue. The residue (430 mg) was chromatographed on 50 g of silica gel which had been equilibrated with chloroform/acetonitrile/methanol/ammonium hydroxide (87.8:10:2:0.2 v/v/v/v), eluting at 2.1 mL/min with the same solvent used for equilibration followed, after collecting sixty five 15 mL fractions, by chloroform/acetonitrile/methanol/ammonium hydroxide (83.6:10:6:0.4 v/v/v/v) to give 275.2 mg (60% yield) of the title compound; DCI/NH$_3$ MS M/Z: 729 (M+H)$^+$; IR (0.15% in CCl$_4$) 3560, 3510, 3460, 1700 and 1625 cm$^{-1}$. [a]$_D$ 22° C.=−58.7° (c 1.00; MeOH).

EXAMPLE 13

Alternate preparation of
[2R-[2R*,3R*(1R*,2R*),6R*,7S*,8S*,9R*, 10R*
]]-7-[(2,6-Dideoxy-
3-C-methyl-3-O-methyl-α-L-ribo-hexopyranosyl)
oxy]-3-(1,2-dihydroxy-1-methyl butyl)-
2,6,8,10,12-pentamethyl-9-[[3,4,6-trideoxy,3-
(dimethylamino)-β-D-xylo-hexopyranosyl]oxy]-4,13-
dioxabicyclo[8.2.1]tridec-12-en-5-one Erythromycin A (30.01 g, 40.89 mmol) was suspended in 200 mL of acetonitrile. To the stirred suspension was added 10.541 g (81.751 mmol) of dichloroacetic acid in 100 mL of acetonitrile over a 20 minute period; the erythromycin dissolved after addition of about half the volume. The reaction was stirred for 2.5 hours at 23° C. giving the enol ether. To the solution containing the enol ether intermediate was added over a 30 minute period a solution of 16.951 g (122.65 mmol) of potassium carbonate dissolved in 300 mL of 1:1 (v/v) methanol:water. The mixture was then refluxed for 1.5 hours, cooled to room temperature and concentrated in vacuo to leave a white residue. The residue was dissolved in a mixture of 200 mL of chloroform, 200 mL of 8% sodium bicarbonate solution and 100 mL of saturated brine. The organic layer was then separated, the aqueous layer extracted with chloroform and the organic layers combined. This solution was washed with a mixture of sodium bicarbonate solution and saturated brine, dried over sodium sulfate, filtered and concentrated to dryness. The residue was dissolved in 100 mL of acetonitrile and evaporated in vacuo to give 28.67 g of crude product as a foam. The material was crystallized from acetonitrile to afford 18.717 g of the title product. A second extraction was performed, and the total yield for the reaction found to be 69%.

EXAMPLE 14

[2R-[2R*,3R*(1R*,2S*6R*,7S*,8S*,9R*,10R*]]-
7-[(2.4.6-Trideoxy-3-methyl-
3-O-methyl-α-L-ribo-hexopyranosyl)oxy]-
3-1,2-epoxy-1-methylbutyl)-2,6,8,10,12,-pentamethyl-
9-[[2-O-acetyl-3,4,6-trideoxy-3,(dimethylamino)-
β-D-xylo-hexopyranosyl]oxy]-
4,13-dioxabicyclo[8.2.1]tridec-12-en-5-one Step 1. [2R-[2R*,3R*(1R*,2S*),6R*,7S*,8S*,9R*, 10R*]]- 7-[(2,6-Dideoxy-3-C-methyl- 3-O-methyl-αL-ribo-hexopyranosyl)oxy]-3-(1,2-epoxy-1-methylbutyl)-2,6,8,10, 12-pentamethyl-9-[[2-O-acetyl-3,4,6-trideoxy-3-(dimethylamino)-β-D-xylo- hexopyranosyl]oxy]-4,13-dioxabicyclo[8.2.1]tridec-12-en-5-one A 3.001 g (4.300 mmol)) sample of [2R-[2R*,3R*(1R*, 2S*),6R*,7S*,8S*, 9R*,-10R*]]-7-[(2,6-Dideoxy-3-C-methyl-3-O-methyl-β-L-ribo-hexopyranosyl)oxy]-3-( 1,2-epoxy-1-methylbutyl)-2,6,8,10,12-pentamethyl-9-[[3,4,6-trideoxy- 3-(dimethylamino)-β-D-xylo-hexopyranosyl]oxy] -4,13-dioxabicyclo[8.2.1]tridec-12-en-5-one (the product of Example 1A, step 2 above) was dissolved in 40 mL of methylene chloride, and 1,2 mL of triethylamine and 0.81 mL of acetic anhydride were added. The reaction was allowed to proceed for 24 hours, whereupon the solvent was removed under vacuum and the residue dissolved in 100 mL of ethyl acetate. The ethyl acetate solution was washed with 8% NaHCO$_3$, 5% NaH$_2$PO$_4$, H$_2$O and 8% NaHCO$_3$ solutions, then dried over sodium sulfate, filtered and taken to dryness. Exhaustive drying yielded 3.175 g of the title product. This material was taken to the next step without further purification.

Step 2. [2R-[2R*,3R*(1R*,2S*),6R*,7S*,8S*,9R*,10R*]]- 7-[(2,6-Dideoxy-3-C-methyl- 3-O-methyl-4-O-imidazolylthiocarbonyl-α-L-ribo-hexopyranosyl)oxy]-3-(1,2epoxy- 1-methylbutyl)-2.6,8,10,12-pentamethyl-9-[[2-O-acetyl-3,4,6-trideoxy- 3-(dimethylamino)-β-D-xylo-hexopyranosyl]oxy]-4,13-dioxabicyclo[8.2.1]tridec-12-en-5-one A 3.109 g sample of the product of Step 1 above, 2.064 g (16.894 mmol) of DMAP and 2.260 g (12.681 mmol) of 1,1'-thiocarbonyldiimidazole (Aldrich) were dissolved in 40 mL of methylene chloride, and the reaction allowed to proceed at 25° C. for 18 hours. To the reaction mixture was then added 1.15 mL of concentrated NH$_4$OH, and the reaction stirred at room temperature for 45 minutes. Next was added 100 mL of 0.5M acetate buffer, followed by 2 mL of acetic acid to adjust the pH to 6.0, and the mixture stirred for 2 hours. Additional solvent was added, and the organic phase separated. After washing first with acetate buffer (pH 4.7), and then with 8% NaHCO$_3$, the solution was dried over sodium sulfate, filtered and taken to dryness to yield 3.357 g of the title compound.

Step 3. [2R-[2R*,3R*(1R*,2S*),6R*,7S*,8S*,9R*,10R*]]-7-[(2,4,6-Trideoxy-3-C-methyl- 3-O-methyl-α-L-ribo-hexopyranosyl)oxy]-3-(1,2-epoxy-1-methylbutyl)-2,6,8,10,12-pentamethyl-9-[[2-O-acetyl-3,4,6-trideoxy-3-(dimethylamino)-β-D-xylo-hexopyranosyl]oxy]-4,13-dioxabicyclo [8.2.1]tridec-12-en-5-one A mixture of 3.319 g (3.905 mmol) of the product of step 2 above and 0.128 g (0.779 mmol) of AIBN (2,2'-azobis(2-methylpropionitrile) was dissolved in 60 mL of dry toluene. To this was added 2.2 mL (6.98 mmol) of tri-n-butyl tin hydride, and the mixture degassed and held under $N_2$ before heating in an oil bath at 100° C. for 1 hour. The mixture was concentrated to a syrup, then dissolved in 100 mL of $CHCl_3$. This solution was washed with acetate buffer (pH 4.7), then with 8% aqueous $NaHCO_3$, dried over $Na_2SO_4$, filtered and taken to dryness to yield 5.653 g of a residue. The residue was dissolved in 200 mL of acetonitrile and washed 3 times with 50 mL portions of hexane. The acetonitrile layer was concentrated to dryness to afford 2.69 g of the title product.

EXAMPLE 15

[2R-(2R*,3R*,4R*,5R*,8R *,9S*, 10S*,11R*,12R*)]-9-[(2,4,6-Trideoxy-3-C-methyl-3-O-methyl-α-L-ribo-hexopyranosyl)oxy]-5-ethyl-3,4-dihydroxy-2,4,8,10,12,14-hexamethyl-11-[[3,4,6-trideoxy-3-(dimethylamino)-β-D-xylo-hexopyranosyl]oxy]-6-aza-15-oxabicyclo[10.2.1]pentadec, 14-en-7-one A 508 mg sample of the product of Example 14 was placed in a 20 mL pressure tube. The sample was dissolved in 10 mL of 15% $NH_3$ in methanol, flushed with $N_2$, sealed and heated at 100° C. in an oil bath for 4 days. The contents of the tube were taken to dryness, and the crude product purified by preparative chromatography on silica gel, eluting with 0.2:2:10:100 $NH_4OH$:methanol:acetonitrile:$CHCl_3$. The solvent was removed from the fractions containing the product to afford 228 mg of the title compound as a glass. MS M/Z 699 (M+H). IR ($CCl_4$): 3520b, 3480b, 3440sh, 3355sh, 1700w, 1662s. $[\alpha]_D$ –33.6° (C=0.50, MeOH, 24° C.). Anal Calc. for $C_{37}H_{66}N_2O_{10}$: C, 63.58; H, 9.52; N, 4.01; Found: C, 63.15; H, 9.48; N, 3.98.

EXAMPLE 16

[2R-(2R*,3R*,4R*,5R*,8R*,9S*,10S*,11R*, 12R*)]-9-[(2,4,6-Trideoxy-3-C-methyl-3-O-methyl-α-L-ribo-hexopyranosyl)oxy]-5-ethyl-3,4-dihydroxy-2,4,6,8,10,12,14-heptamethyl-11-[[3,4,6-trideoxy-3-(dimethylamino)-β-D-xylo-hexopyranosyl]oxy]- 6 -aza-15-oxabicyclo[10.2.1]pentadec-14-en-7-one A 607.2 mg sample of the product of Example 14 was placed in a 20 mL pressure tube, and 10 mL of 15% methylamine in methanol was added. The tube was flushed with $N_2$, sealed and heated at 100° C. in an oil bath for 4 days. The tube was opened, and the solvent removed to yield 634 mg of crude product. This material was purified by chromatography on silica gel, eluting with 0.2:2:10:100 $NH_4OH$:methanol:acetonitrile:$CHCl_3$. The solvent was removed from the fractions containing the product to afford 302.4 mg of the title compound as a glass. $[\alpha]D$=–55.0° (C=1.00, MeOH, 29° C.). IR ($CCl_4$): 3510b, 3460b, 1700w, 1622s $cm^{-1}$. Anal Calc. for $C_{38}H_{68}N_2O_{10}$: C, 64.02; H, 9.61; N, 3.93; Found: C, 64.02;H, 9.67; N, 3.92.

EXAMPLE 17

-[2R-(2R*,3R*,4R*,5R*,8R*, 9S*,10S*,11R*,12R*)]-9- [( 2.6-Dideoxy-3-C-methyl-3-O-methyl-α-L-ribo-hexopyranosyl)oxy]-5-ethyl-3,4-dihydroxy-2,4,8,10,12,14-hexamethyl-11-[[3,4,6-trideoxy-3-(n-butylmethylamino)-β-D-xylo-hexopyranosyl]oxy]-6-aza-15-oxabicyclo[10.2.1]pentadec-14-en-7-one To a heavy-walled flask (Parr Instrument Co.) were added 311 mg of the product of Example 4,30 mL of methanol, 120 mg of 10% Pd/C and 0.30 mL of butyraldehyde. The flask was charged with 4 atm of hydrogen and shaken for 16 hours. The catalyst was removed by filtration, and the solvent was removed under vacuum. The residue was dissolved in acetonitrile and taken to dryness twice to give 340 mg of crude product. The crude product was purified by reverse phase HPLC, eluting with 40:60 acetonitrile:water containing 10 g/L of ammonium acetate. The eluent fractions were concentrated to half their volume and were made alkaline by the addition of 1N NaOH in small portions. The product was extracted into chloroform which was washed with 8% aqueous $NaHCO_3$, dried over sodium sulfate, filtered and concentrated. The residue was dissolved in acetonitrile which was then removed under vacuum to yield 170.6 mg of the title product as a glass. MS M/Z 757 (M+H). $[\alpha]D$=–32.9° (c=1.00, methanol, 28° C.). IR ($CCl_4$): 3560, 3520, 3440, 1702, 1660 $cm^{-1}$. Anal Calc. for $C_{40}H_{72}N_2O_{11}$: C, 63.46; H, 9.59; N, 3.70; Found: C, 62.95; H, 9,48; N, 3.63.

EXAMPLE 18

[2R-(2R*,3R*,4R*,5R*,8R*, 9S*,10S*,11 R*,12R*)]-9-[( 2,6-Dideoxy-3-C-methyl-3-O-methyl-α-L-ribo-hexopyranosyl)oxy]-5-ethyl-3.4-dihydroxy-2,4,8,10,12,14-hexamethyl-11-[[3,4,6-trideoxy-3-(n-propylmethylamino)-β-D-xylo-hexopyranosyl]oxy]-6-aza-15-oxabicyclo[10.2.1]pentadec-14-en-7-one By a procedure similar to that described in Example 17, 382 mg of the product of Example 4 was reacted with propionaldehyde instead of butyraldehyde, to afford 196.2 mg of the title compound as a white glass. MS M/Z 743 (M+H). $[\alpha]D$=–32.8° (c=1.00, methanol, 28° C.). Anal Calc. for $C_{39}H_{70}N_2O_{11}$: C, 63.05; H, 9.50; N, 3.79; Found: C, 63.05; H, 9.50; N, 3.79.

EXAMPLE 19

[2R-(2R*,3R*,4R*,5R*,8R*,9S*,10S*,11 R *.12R*)]- 9-[(2,6-Dideoxy-3-C-methyl-3-O-methyl-α-L-ribo-hexopyranosyl)oxy]-5-ethyl-3,4-dihydroxy-2,4,8,10,12,14-hexamethyl-11-[[3,4,6-trideoxy-3-(i-propylmethylamino)-β-D-xylo-hexopyranosyl]oxy]-6-aza-15-oxabicyclo [10.2.1]pentadec-14-en-7-one In a 20 mL pressure tube were placed 200 mg of the product of Example 4, 0.5 mL of diisopropylethylamine, 1.0 mL of 2-iodopropane and 2.0 mL of acetonitrile. The tube was flushed with $N_2$ sealed and heated at 70° C. in an oil bath. For workup, the products of two such runs were combined. The solvents were remove, and the residue was dissolved in a mixture of 30 mL ethyl acetate, 20 mL of 8% aqueous $NaHCO_3$ and 100 mg of sodium thiosulfate. The organic layer was washed, dried and filtered, to give 354 mg of crude product. The crude product was purified by HPLC by a procedure similar to that described in Example 19 to afford 196.2 mg of the title compound as a white glass. MS M/Z 781 (M+H). $[\alpha]D=-32.8°$ (c=1.00, methanol, 27° C.). Anal Calc. for $C_{39}H_{70}N_2O_{11}$: C, 63.05; H, 9.50; N, 3.79; Found: C, 62.54; H, 9.50; N, 3.77.

EXAMPLE 20

[2R-(2R*,3R*,4R*,5R*,8R*,9S*,
10S*,11R*,12R*)]-9-[(2,6-Dideoxy-3-C-methyl-
3-O-methyl-α-L-ribo-hexopyranosyl)oxy]-5-
ethyl-3,4-dihydroxy-2,4,8,10,12,14-hexamethyl-
11-[[3,4,6-trideoxy-3-(i-butylmethylamino)-β-
D-xylo-hexopyranosyl]oxy]-6-aza,
15-oxabicyclo[10.2.1]pentadec-14-en-7-one By a procedure similar to that described in Example 19, 400 mg of the product of Example 4 were reacted with 2-iodobutane instead of 2-iodopropane to afford, after purification by HPLC, two samples (the N-(S)-2-butyl and N-(R)-2-butyl isomers).

21a. (S-isomer): 134 mg; MS M/Z 757 (M+H). $[\alpha]D=-30.2°$ (c=0.5, methanol, 27° C.). IR 3560, 3440, 3350, 1700, 1658 $cm^{-1}$.

21b. (R-isomer): 112.5 mg; MS M/Z 757 (M+H). $[\alpha]_D=-36.4°$ (C=0.5, methanol, 27° C). IR 3560, 3440, 3350, 1700, 1659 $cm^{-1}$.

EXAMPLE 21

In Vitro Assay of Gastric Prokinetic Activity

The compounds of the present invention were tested in vitro for their ability to induce contraction of smooth muscle strips isolated from rabbit small intestine using the following procedure.

Rabbits were sacrificed and 15 cm of duodenum was rapidly removed and placed in ice-cold modified Ringers solution (120 mM sodium chloride, 25 mM sodium bicarbonate, 4.7 mM potassium chloride, 1.25 mM calcium chloride, 1.20 mM magnesium sulfate and 5.6 mM glucose). The longitudinal muscle layer was separated from the circular muscle by blunt dissection and cut into strips of 10×20 mm. Double-folded strips were vertically suspended between two hooks in 10 mL tissue baths with a mechanical preload of 1 g. The upper hook was connected to an isotonic force transducer, and its displacement was recorded on a Grass polygraph. The tissue baths contained modified Ringers solution at 37° C. and were continuously gassed with 95% oxygen/5% carbon dioxide in order to maintain the pH at 7.5.

After a stabilization period of at least 60 minutes, a contractility dose-response series was performed by adding increasing final concentrations of methacholine ($10^{-7}M$, $10^{-6}M$ and $10^{-5}M$) in volumes of 100 μL. The bath solutions were replaced at least three times between doses.

After the methacholine dose-response series was completed, a test compound dose response curve was initiated by the same procedure used for the methacholine dose-response series, with at least five concentrations of test compound within the range of $10^{-10}M$ to $10^{-4}M$. The tissues were washed repeatedly between doses, and the studies were completed by recording the contractile response to $10^{-5}M$ methacholine to ascertain integrity of the muscle preparation. Contractile responses were expressed as percent of maximal contraction. The concentration of test compound which produces half of the maximal contraction (ED50 value) and the negative logarithm of the $ED_{50}$ value ($pED_{50}$) were estimated from the dose-response curves. The $pED_{50}$ values are shown in Table 1 in comparison to erythromycin A which is a known gastrointestinal prokinetic agent. From these data it is evident that the compounds of the present invention are potent prokinetic agents.

TABLE 1

| In Vitro Rabbit Duodenal Smooth Muscle Contraction Assay | | |
|---|---|---|
| Example Number | $pED_{50}$ (−log M) | Relative Potency |
| 1 | 7.10 | 18.0 |
| 3 | 7.50 | 45.0 |
| 4 | 6.50 | 5.0 |
| 5 | 7.10 | 18.0 |
| 7 | 6.60 | 5.6 |
| 8 | 6.30 | 3.0 |
| 9 | 6.25 | 2.5 |
| 10 | 6.10 | 1.8 |
| 12 | 7.22 | 23.4 |
| 15 | 8.27 | 263 |
| 16 | 8.50 | 447 |
| 17 | 5.67 | 0.66 |
| 18 | 6.00 | 1.41 |
| 19 | 7.63 | 60.3 |
| 20 (S) | 8.40 | 355 |
| 20 (R) | 9.27 | 2630 |
| erythromycin A | 5.85 | 1.0 |

EXAMPLE 22

Gastrointestinal Prokinetic Activity: In Vivo Assay in Anesthetized Dogs

The compounds of the present invention were tested in vivo for their ability to induce gastrointestinal motility using the following procedure: Adult female beagle dogs, food deprived for 16–20 hours and weighing between 7.0 and 12.0 kg, were anesthetized with 30 mg/kg of sodium pentobarbital given intravenously. Anesthesia was maintained during the experimental procedure by continuous intravenous infusion of 5 mg/kg Nembutal in 0.9% saline. After tracheal intubation, the animals were mechanically respired with a Harvard positive pressure respiratory pump. Rectal temperature was maintained at 37° C. by a heated animal table. A polyethylene catheter was inserted into the right femoral artery to record blood pressure and heart rate using a Steatham P23 pressure transducer. Polyethylene catheters were also introduced into the right femoral vein for infusion of anesthetic and the left femoral vein for drug administration and blood samples. The abdomen was opened by a midline incision immediately below the xiphoid process extending to 2 cm below the umbilicus.

Five strain-gauge transducers were used to monitor contractile activity of the circular muscle layer of the stomach or intestine. Each was calibrated to give a 60% full scale deflection when supporting a 100 g weight between two planar surfaces. However, due to variability in transducer response, output when applied to the circular muscle layer was observed to vary despite the first stage of calibration. Therefore, final sensitivity adjustments were subsequently made with transducers sewn in place to yield comparable deflections of paired transducers. Two transducers were sutured to the serosal surface of the antrum of the stomach. The first was approximately 5 cm proximal to the pylorus and the second 1 cm proximal to the first. Two transducers were also sutured to the duodenum; they were approximately 12 cm distal to the pylorus and about 1 cm apart. Only one transducer was sutured to the jejunum, approximately 10 cm from the ligament of Treitz, and was not pair calibrated. Two transducers were used in both the stomach and duodenum to minimize variability. After application of the transducers, the abdominal wound was closed and gastrointestinal motility patterns were allowed to stabilize for from 45 to 90 minutes before drug administration.

Motility and blood pressure were recorded by a Grass Model 7 oscillograph. The records were manually analyzed by a scoring system which included both magnitude and duration of muscular contractions. The manual scoring system consisted of pulse-height measurement by counting recorded contractile waves in relation to five selected amplitudes (7, 17, 34, 68, 136, >136 g). A transparent guide was used to facilitate scoring. A minimal pulse-height score was assigned for every contraction between each of these levels (a score of 0.5 for all contractions between 7 and 17 g, a score of 1.0 for contractions between 17 and 34 g, a score of 2.0 for contractions between 34 and 68 g, a score of 4.0 for contractions between 68 and 136 g and a score of 8.0 for contractions over 136 g). Scores were computed for the 60 minute period following drug administration. Mean scores were computed for the two transducers in both stomach and duodenum. Drugs were administered for either 2 or 3 periods, each period consisting of 90 minutes. In period 1, the test compound was typically administered and motility responses recorded for 60 minutes. In period 2, erythromycin A lactobionate was then administered to establish an internal control for each animal studied. All compounds for one experiment were given at the same dose, usually 4.0 mg/kg.

Several experiments were done with erythromycin A lactobionate alone. Erythromycin was administered in both periods and the data analyzed in the standard manner. Due to dose-dependent tachyphylaxis, a motility response induced by erythromycin in period 1 resulted in reduced erythromycin response in period 2. Test compounds should ideally be investigated by both prior and subsequent administration with respect to erythromycin dosing to minimize tachyphylactic bias. For initial screening, however, the standard protocol was test compound (period 1) followed by erythromycin (period 2).

The final expression of results was a ratio between the motility scoring for the test compound (period 1) and erythromycin A lactobionate (period 2). For stomach, duodenum and jejunum, the motility score in response to the test compound was divided by the motility score for erythromycin. From these three ratios, an arithmetic mean ratio for "overall motility index" was calculated in which contributions from the three tissue areas measured were weighted equally. The compound of Example 1, when tested in vivo as described above, exhibited a motility index of 19.9 compared to erythromycin A, which was assigned a motility index of 1, demonstrating that the compounds of the invention exhibit potent gastrointestinal prokinetic activity in vivo.

We claim:

1. A compound having the formula

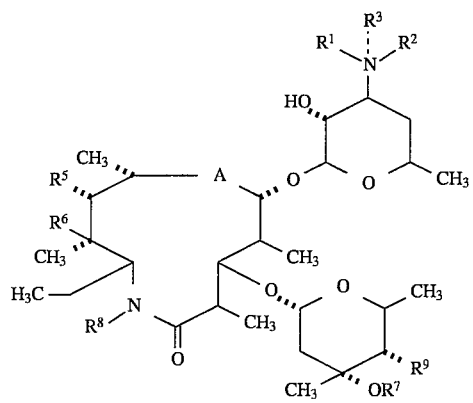

or a pharmaceutically acceptable salt thereof, wherein the dotted line is an optional bond;

A is selected from the group consisting of

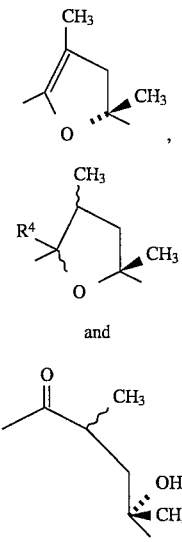

and

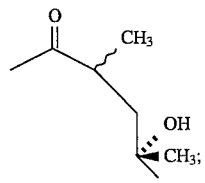

$R^1$ and $R^2$ are independently selected from the group consisting of hydrogen, loweralkyl, halo-substituted loweralkyl, cyano-substituted loweralkyl, hydroxy-substituted loweralkyl, loweralkenyl, loweralkynyl, lower cycloalkyl, lower cycloalkylmethyl and benzyl;

$R^3$ is absent or is selected from the group consisting of loweralkyl, loweralkenyl, loweralkynyl and benzyl and accompanied by a pharmaceutically acceptable counterion so as to form a quaternary ammonium salt;

$R^4$ is hydrogen; or $R^4$ and $R^6$ taken together represent oxygen;

$R^5$ is selected from the group consisting of —OH and —OR$^{10}$, wherein R$^{10}$, is selected from loweralkyl, loweralkanoyl and —S(O)$_2$CH$_3$; or $R^5$ and $R^6$ taken together form the structure

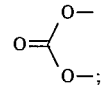

$R^6$ is selected from the group consisting of hydrogen, —OH and —OR$^{11}$ wherein $R^{11}$ is selected from loweralkyl, loweralkanoyl and —S(O)$_2$CH$_3$; or $R^6$ and $R^4$ taken together represent oxygen; or $R^6$ and $R^5$ taken together form the structure

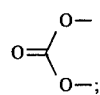

R⁷ is selected from the group consisting of hydrogen and methyl;

R⁸ is selected from the group consisting of hydrogen and loweralkyl; and

R⁹ is selected from the group consisting of hydrogen and hydroxy.

2. A compound according to claim 1 wherein A is

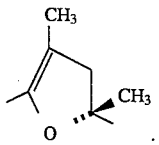

3. A compound according to claim 1 wherein A is

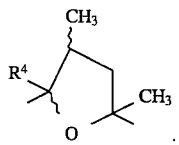

4. A compound according to claim 3 wherein R⁵ and R⁶ form the structure:

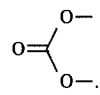

5. A compound according to claim 3 wherein R⁴ and R⁶ taken together represent oxygen.

6. A compound according to claim 1 wherein the compound is selected from the group consisting of

[2R-(2R*, 3R*,4R*,5R*, 8R*,9S*,10S*,11 R*,12R*)]- 9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(dimethylamino)-β-D-xylo-hexopyranosyl]oxy]- 6-aza-15-oxabicyclo[10.2.1]pentadec-14-en-7-one ("erythromycin A lactam enol ether");

[2R-(2R*,3S*,4S*,5R*,8R*, 9S*,10S*,11R*,12R*)]- 9-[(2,6-Dideoxy-3-C-methyl-3-O-methyl-α-L-ribo-hexopyranosyl)oxy]- 5-ethyl-3-hydroxy-2,4,8,10,12,14-hexamethyl- 11-[[3,4,6-trideoxy-3-(dimethylamino)-β-D-xylo-hexopyranosyl]oxy]- 6-aza-15oxabicyclo[10.2.1]pentadec-14-en-7-one ("erythromycin B lactam enol ether");

[2R-(2R*,3R*,4R*,5R*, 8R*,9S*,10S*,11R*,12R*)]- 9-[(2,6-Dideoxy-3-C-methyl- 3-O-methyl-α-L-ribo-hexopyranosyl)oxy]- 5-ethyl-3,4-dihydroxy-2,4,8, 10, 12, 14-hexamethyl- 11-[[3,4,6-trideoxy-3-(methylamino)-β-D-xylo-hexopyranosyl]oxy]- 6-aza- 15-oxabicyclo[10.2.1]pentadec-14-en-7-one;

[2R-(2R*,3R*,4R*,5R*, 8R*,9S*,10S*,11R*,12R*)]- 9-[(2,6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(ethylmethylamino)-β-D-xylo-hexopyranosyl]oxy]6-aza- 15-oxabicyclo[10.2.1]pentadec-14-en-7-one;

[2R-(2R*,3R*,4R*, 5R*,8R*,9S*,10S*,11R*,12R*)]- 9-[(2,6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(methyl(2-propenyl)amino)-β-D-xylo-hexopyranosyl]oxy]-6-aza-15-oxabicyclo[10.2.1]pentadec-14-en-7-one;

[2R-(2R*,3R*,4R*,5R*, 8R*,9S*,10S*,11R*,12R*)]- 9-[(2,6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(dimethyl(2-propenyl)ammonium)-β-D-xylo-hexopyranosyl]oxy]-6-aza-15-oxabi-cyclo[10.2.1]pentadec-14-en-7-one bromide;

[2R-(2R*,3R*,4R*,5R*, 8R*9S*,10S*,11R*,12R*)]- 9-[(2, 6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(dimethylamino)-β-D-xylo-hexopyranosyl]oxy]- 6-aza-15-oxabicyclo[10.2.1]pentadec-14-en-7-one 13-O-14-O-carbonate;

[1R-(1R*2R*,3R*,4R*,5R*, 8R*,9S*,10S*,11R*,12R*,14 S*)]- 9-[(2,6-Dideoxy-3-C-methyl- 3-O-methyl-α-L-ribo-hexopyranosyl)oxy]-5-ethyl-3,4-dihydroxy-2,4,8, 10,12,14-hexamethyl-11-[[3,4,6-trideoxy-3-(dimethylamino)-β-D-xylo-hexopyranosyl]oxy]-6-aza-15-oxabicyclo[10.2.1]pentadecan-7-one;

[1R-(1R*,2R*,3R*,4R*,5R*, 8R*,9S*,10S*,11R*,12R*,14 R*)]- 9-](2,6-dideoxy-3-C-methyl- 3-O-methyl-α-L-ribo-hexopyranosyl)oxy]-5-ethyl-3-hydroxy2,4,8,10,12,14-hexamethyl- 11-[[3,4,6-trideoxy-3-(dimethylamino)-β-D-xylo-hexopyranosyl]oxy]- 6-aza-15,16-dioxatricyclo[10.2.1.1¹,⁴]pentadecan-7-one;

[3R-(3R*,4S*,5S*, 6R*,7R*,9R*,11 R*,12R*, 13R*,14 R*)]-4-[(2,6-dideoxy-3-C-methyl- 3-O-methyl-α-L-ribo-hexopyranosyl)oxy]-14-ethyl-7,12,13-trihydroxy-3,5,7,9, 11,13 -hexamethyl- 6-[[3,4,6-trideoxy-3-(dimethylamino)-β-D-xylo-hexopyranosyl]oxy] azacyclotetradecane-2,10-dione ("erythromycin A lactam");

[2R-(2R*,3R*,4R*,5R*, 8R*,9S*,10S*,11R*,12R*)]- 9-[(2,6-Dideoxy-3-C-methyl-α-L-ribo-hexopyranosyl)oxy]- 5-ethyl-3,4-dihydroxy-2,4,8,10,12,14-hexamethyl-11-[[3,4,6-trideoxy-3-(dimethylamino)-β-D-xylo-hexopyranosyl]oxy]-6-aza-15oxabicyclo[10.2.1]pentadec-14-en-7-one ("erythromycin C lactam enol ether");

[2R-(2R*,3R*,4R*,5R*, 8R*,9S*,10S*,11R*,12R*)]- 9-[(2,6-Dideoxy-3-C-methyl-α-L-ribo-hexopyranosyl)oxy]- 5-ethyl-3,4-dihydroxy-2,4,8,10,12,14-hexamethyl-11-[[3,4,6-trideoxy-3-(ethylmethylamino)-β-D-xylo-hexopyranosyl]oxy]-6-aza-15oxabicyclo[10.2.1]pentadec-14-en-7-one;

[2R-(2R*,3S*,4S*,5R*, 8R*,9S*,10S*,11R*,12R*)]- 9-[(2, 6-Dideoxy-3-C-methyl-α-L-ribo-hexopyranosyl)oxy]-5-ethyl-3-hydroxy-2,4,8,10,12,14-hexamethyl-11-[[3,4, 6-trideoxy- 3-(dimethylamino)-β-D-xylo-hexopyranosyl]oxy]-6-aza-15oxabicyclo[10.2.1]pentadec-14-en-7-one ("erythromycin D lactam enol ether");

[2R-(2R*,3S*,4S*,5R*, 8R*,9S*,10S*,11R*,12R*)]- 9-[(2, 6-Dideoxy-3-C-methyl-α-L-ribo-hexopyranosyl)oxy]-5-ethyl-3-hydroxy-2,4,8,10,12,14-hexamethyl-11-[[3,4, 6-trideoxy- 3-(ethylmethylamino)-β-D-xylo-hexopyranosyl]oxy]-6-aza-15oxabicyclo[10.2.1]pentadec-14-en-7-one;

[2R-(2R*,3R*,4R*,5R*, 8R*,9S*,10S*,11R*,12R*)]- 9-[(2,6-Dideoxy-3-C-methyl-3-O-methyl-α-L-ribo-hexopyranosyl)oxy]- 5-ethyl-3,4-dihydroxy-2,4,6,8,10,12, 14-heptamethyl- 11-[[3,4,6-trideoxy-3-(dimethylamino)-β-D-xylo-hexopyranosyl]oxy]- 6 -aza-15-oxabicyclo[10.2.1]pentadec-14-en-7-one;

[2R-[2R*,3R*(1R*,2S*), 6R*,7S*,8S*,9R*,10R*]]- 7-[(2, 4,6-Trideoxy-3-C-methyl- 3-O-methyl-α-L-ribo-hexopyranosyl)oxy]-3-(1,2-epoxy-1-methylbutyl)-2,6,8,10,12-pentamethyl- 9-[[2-O-acetyl-3,4,6-trideoxy-3-(dimethylamino)-β-D-xylo-hexopyranosyl]oxy]-4,13-dioxabicyclo[8.2.1]tridec-12-en-5-one;

[2R-(2R*,3R*,4R*,5R*,8R*,9S*,10S*,11R*,12R*)]- 9-[(2, 4,6-Trideoxy-3-C-methyl- 3-methyl-α-L-ribo-hexopyranosyl)oxy]-5-ethyl-3,4-dihydroxy-2,4,8,10,12,14-hexamethyl- 11-[[3,4,6-trideoxy-3-(dimethylamino)-β-D-xylo-hexopyranosyl]oxy]- 6-aza-15oxabicyclo[10.2.1]pentadec-14-en-7-one;

[2R-(2R*,3R*,4R*,5R*,8R*,9S*,10S*,11R*,12R*)]- 9-[(2, 4,6-Trideoxy-3-C-methyl- 3-methyl-α-L-ribo-hexopyranosyl)oxy]-5-ethyl-3,4-dihydroxy-2,4,6,8,10,12,14-heptamethyl- 11-[[3,4,6-trideoxy-3-(dimethylamino)-β-D-xylo-hexopyranosyl]oxy]- 6-aza-15-oxabicyclo[10.2.1]pentadec-14-en-7-one;

[2R-(2R*,3R*,4R*,5R*,8R*,9S*,10S*,11R*,12R*)]- 9-[(2, 6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(n-butylmethylamino)-β-D-xylo-hexopyranosyl]oxy]- 6-aza- 15-oxabicyclo[10.2.1]pentadec-14-en-7-one;

[2R-(2R*,3R*,4R*,5R*,8R*,9S*,10S*,11R*,12R*)]- 9-[(2, 6-Dideoxy-3-C-methyl-3-O-methyl-α-L-ribo-hexopyranosyl)oxy]- 5-ethyl-3,4-dihydroxy-2,4,8,10,12,14-hexamethyl- 11-[[3,4,6-trideoxy-3-(n-propylmethylamino)-β-D-xylo-hexopyranosyl]oxy]-6-aza- 15-oxabicyclo[10.2.1]pentadec-14-en-7-one;

[2R-(2R*,3R*,4R*,5R*,8R*,9S*,10S*,11R*,12R*)]- 9-[(2, 6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(i-propylmethylamino)-β-D-xylo-hexopyranosyl]oxy]-6-aza-15-oxabicyclo[10.2.1]pentadec-14-en-7-one; and

[2R-(2R*,3R*,4R*,5R*,8R*,9S*,10S*,11R*,12R*)]- 9-[(2, 6-Dideoxy-3-C-methyl- 3-O-methyl-α-L-ribo-hexopyranosyl)oxy]-5-ethyl-3,4-dihydroxy-2,4,8,10,12,14-hexamethyl- 11-[[3,4,6-trideoxy-3-(i-butylmethylamino)-β-D-xylo-hexopyranosyl]oxy]-6-aza-15-oxabicyclo[10.2.1]pentadec-14-en-7-one;

and pharmaceutically acceptable salts thereof.

7. A pharmaceutical composition comprising a therapeutically effective amount of a prokinetic compound according to claim 1 and a pharmaceutically acceptable carrier.

* * * * *

UNITED STATES PATENT AND TRADEMARK OFFICE
CERTIFICATE OF CORRECTION

PATENT NO. : 5,538,961
DATED : July 23, 1996
INVENTOR(S) : Freiberg, et. Al.

It is certified that error appears in the above-indentified patent and that said Letters Patent is hereby corrected as shown below:

Column 53, line 41, change "11  R*" to --11R*--.

Column 53, line 53, change "15oxabicyclo" to --15-oxabicyclo--.

Column 54, line 54, change "15oxabicyclo" to --15-oxabicyclo--.

Column 54, line 60, change "15oxabicyclo" to --15-oxabicyclo--.

Column 55, line 8, change "3-methyl" to --3-O-methyl--.

Column 55, line 11, change "15oxabicyclo" to --15-oxabicyclo--.

Column 55, line 14, change "3-methyl" to --3-O-methyl--.

Signed and Sealed this

First Day of July, 1997

*Attest:*

BRUCE LEHMAN

*Attesting Officer*     *Commissioner of Patents and Trademarks*